US008343492B2

(12) United States Patent
Hardiman et al.

(10) Patent No.: US 8,343,492 B2
(45) Date of Patent: *Jan. 1, 2013

(54) METHOD FOR BLOCKING BINDING OF CX3C CHEMOKINES USING CX3C CHEMOKINE ANTIBODIES

(75) Inventors: Gerard T. Hardiman, San Diego, CA (US); Devora L. Rossi, San Diego, CA (US); Kevin B. Bacon, Kobe (JP); J. Fernando Bazan, Palo Alto, CA (US); Thomas J. Schall, Menlo Park, CA (US); Albert Zlotnik, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,224

(22) Filed: Apr. 23, 2012

(65) Prior Publication Data

US 2012/0225482 A1 Sep. 6, 2012

Related U.S. Application Data

(60) Division of application No. 12/833,069, filed on Jul. 9, 2010, now Pat. No. 8,173,117, which is a continuation of application No. 12/510,586, filed on Jul. 28, 2009, now Pat. No. 7,785,804, which is a continuation of application No. 12/198,626, filed on Aug. 26, 2008, now Pat. No. 7,585,502, which is a continuation of application No. 11/495,801, filed on Jul. 28, 2006, now Pat. No. 7,431,924, which is a continuation of application No. 10/397,559, filed on Mar. 25, 2003, now Pat. No. 7,115,379, which is a division of application No. 09/771,023, filed on Jan. 25, 2001, now Pat. No. 6,566,503, which is a division of application No. 09/093,482, filed on Jun. 8, 1998, now abandoned, which is a division of application No. 08/786,068, filed on Jan. 21, 1997, now abandoned, which is a continuation of application No. 08/649,006, filed on May 16, 1996, now Pat. No. 6,548,654, which is a continuation of application No. 08/590,828, filed on Jan. 24, 1996, now abandoned.

(51) Int. Cl.
*A61K 39/395* (2006.01)
(52) U.S. Cl. ............... 424/139.1; 424/130.1; 424/134.1
(58) Field of Classification Search ................. None
See application file for complete search history.

(56) References Cited

U.S. PATENT DOCUMENTS

| 6,013,257 | A | 1/2000 | Pan |
| 6,043,086 | A | 3/2000 | Pan |
| 6,548,654 | B1 | 4/2003 | Hardiman et al. |
| 6,566,503 | B2 | 5/2003 | Hardiman et al. |
| 7,115,379 | B1 | 10/2006 | Hardiman et al. |
| 7,431,924 | B2 | 10/2008 | Hardiman et al. |

FOREIGN PATENT DOCUMENTS

WO WO97/42224 11/1997

OTHER PUBLICATIONS

Kevin B. Bacon et al., Int. Arch. Allergy Immunol., 109:97-109, 1996. "Chemokines as Mediators of Allergic Inflammation".
J. Fernando Bazan et al., Nature, 385:640-644, Feb. 13, 1997. A new class of membrane-bound chemokine with a $CX_3C$ motif.
D. Beier et al., Genbank Accession No. R75309, p. 1, Jun. 6, 1995.
Mark S. Boguski, Trends Biochem. Sci. (TIBS), 20:295-296, 1995. "The turning point in genome research".
Myriam C. Capone et al., J. Immunol., 157:969-973, 1996. "Identification Through Bioinformatics of cDNAs Encoding Human Thymic Shared Ag-1/Stem Cell Ag-2: A New Member of the Human Ly-6 Family.sup.1,2".
Angela M. Gronenborn et al., Protein Engineering, 4(3):263-269, 1991. "Modeling the Three-Dimensional Structure of the Monocyte Chemo-Attractant and Activating Protein MCAF/MCP-1 on the Basis of the Solution Structure of Interleukin-8".
L. Hillier et al., Genbank Accession No. H06104, pp. 1-2, Jun. 21, 1995.
Patricia J. Lodi et al., Science, 263:1762-1767, 1994. "High-Resolution Solution Structure of the .beta. Chemokine hMIP-1.beta. by Multidimensional NMR,".
Kouji Matsushima et al., Cytokine, 1(1):2-13, 1989. "Interleukin 8 and MCAF: Novel Inflammatory Cytokines Inducible by IL 1 and TNF".
Michael D. Miller et al., Proc. Natl. Acad. Sci., 89:2950-2954, 1992. "The Human Cytokine I-309 is a Monocyte Chemoattractant".
Joost J. Oppenheim et al., Annu. Rev. Immunol., 9:617-648, 1991. "Properties of the Novel Proinflammatory Supergene 'Intercrine' Cytokine Family".
Thomas J. Schall, The Cytokine Handbook, Angus W. Thompson, Ed., 2nd ed. The Academic Press Limited, Ch. 22, pp. 419-460, 1994. "The Chemokines".
Thomas J. Schall et al., Current Opinion in Immunol., 6:865-873, 1994. "Chemokines, Leukocyte Trafficking, and Inflammation".
Thomas J. Schall, Cytokine, 3(3):165-183, 1991. "Biology of the RANTES/SIS Cytokine Family".
Mark Y. Stoeckle et al., The New Biologist, 2(4):313-323, 1990. "Two Burgeoning Families of Platelet Factor 4-Related Proteins: Mediators of the Inflammatory Response".
Steven R. Wiley et al., Immunity, 3: 673-682, 1995. "Identification and Characterization of a New Member of the TNF Family that Induces Apoptosis".
D. Rossi et al., FASEB Journal, 10(6):A1049, Abstract No. 290, from Joint Meeting of the American Society for Biochemistry and Molecular Biology, The American Society for Investigative Pathology and the American Association of Immunologists, New Orleans, LA, USA Jun. 1996. "Identification of a .gamma. or "C" chemokine from the chicken and a novel human and mouse chemokine".
L. Hillier et al., EMBL Database Entry HS940163, Accession No. H14940, Jul. 3, 1995, XP002030088. "The WashU-Merck EST project".

(Continued)

*Primary Examiner* — Prema Mertz

(57) ABSTRACT

Nucleic acids encoding a new family of chemokines, the CX3C family, from a mammal, reagents related thereto, including specific antibodies, and purified proteins are described. Methods of using said reagents and related diagnostic kits are also provided.

6 Claims, No Drawings

OTHER PUBLICATIONS

C. Auffray et al., EMBL Database Entry HSC20F041, Accession No. Z44443, Sep. 21, 1995, XP002030091. "Image: Integrated molecular analysis of the human genome and its expression".

Fiorenza Cocchi et al., Science, 270:1811-1815, Dec. 15, 1995. "Identification of RANTES, MIP-1.alpha., and MIP-1-.beta. as the Major HIV-Suppressive Factors Produced by CD8.sup.+ T Cells".

Derwent Geneseq Patent Sequence Database, Accession No. 97P-W34307, citing: WO 9742224 A1 dated Nov. 13, 1997, US 97-851160 dated May 5, 1997; US 96-643798 dated May 7, 1997; "Search record pertaining to human CX3C chemokine, performed in Jul. 1998".

Derwent Geneseq Patent Sequence Database, Accession No. 19P-W23345, citing: WO 9727299 A1 dated Jul. 31, 1997; WO 97-US293 dated Jan. 23, 1997; US 96-649006 dated May, 16, 1996; US 96-590828 dated Jan. 24, 1996; "Search record pertaining to human CX3C chemokine, performed in Jul. 1998".

Derwent Geneseq Patent Sequence Database, Accession No. 97P-W34308, citing: WO 9742224 A1 dated Nov. 13, 1997; WO 97-US7737 dated May 6, 1997; US 97-851160 dated May 5, 1997; US 96-643798 dated May 7, 1996; "Search record pertaining to human CX3C chemokine, performed in Jul. 1998".

Derwent Geneseq Patent Sequence Database, Accession No. 19P-W23347, citing: WO 9727299 A1 dated Jul. 31, 1997; WO 97-US293 dated Jan. 23, 1997; US 96-649006 dated May 16, 1996; US 96-590828 dated Jan. 24, 1996; "Search record pertaining to human CX3C chemokine, performed in Jul. 1998".

Derwent Geneseq Patent Sequence Database, Accession No. 19P-W23344, citing: WO 9727299 A1 dated Jul. 31, 1997; WO 97-US293 dated Jan. 23, 1997; US 96-6496006 dated Jan. 6, 1996; US 96-590828 dated Jan. 24, 1996; "Search record pertaining to human CX3C chemokine, performed in Jul. 1998".

Derwent Geneseq Patent Sequence Database, Accession No. 19P-W23346, citing: WO 9727299 A1 dated Jul. 31, 1997; WO 97-US293 dated Jan. 23, 1997; US 96-649006 dated May 16, 1996; US 96-590828 dated Jan. 24, 1996; "Search record pertaining to human CX3C chemokine, performed in Jul. 1998".

Derwent Geneseq Patent Sequence Database, Accession No. 98P-W42072, citing: WO 9802459 A1 dated Jan. 22, 1998; WO 97-US12349 dated Jul. 15, 1997; US 96-683655 dated Jul. 15, 1996; "Search record pertaining to human CX3C chemokine, performed in Jul. 1998".

Derwent Geneseq Patent Sequence Database, Accession No. 97P-W26655, citing: WO 9725427 A1 dated Jyl. 17, 1997; WO 97-US379 dated Jan. 10, 1997; US 96-586395 dated Jan. 12, 1996; "Search record pertaining to human CX3C chemokine, performed in Jul. 1998".

James U. Bowie et al., Science, 247: 1306-1310, Mar. 16, 1990. "Deciphering the Message in Protein Sequences: Tolerance to Amino Acid Substitutions".

Claude Daniel et al., Virology, 202:540-549, 1994. "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier".

C. Frommel et al., J. Mol. Evol., 21:233-257, 1985. "An Estimate on the Effect of Point Mutation and Natural Selection on the Rate of Amino Acid Replacement in Proteins".

David G. George et al., Macromolecular Sequencing and Synthesis, David H. Schlesinger, Ed., Chapter 12, pp. 127-149, Alan R. Liss, Inc.: New York 1988. "Current Methods in Sequence Comparison and Analysis".

Minoru Kanehisa, Nucleic Acids Research, 12(1):203-213, 1984. "Use of statistical criteria for screening potential homologies in nucleic acid sequences".

J. Thomas Ngo et al., The Protein Folding Problem and Tertiary Structure Prediction, K. Mertz, Jr. and S. Le Grand, Eds., Chapter 14, pp. 491-495, Birkhauser: Boston 1994. "Computational Complexity, Protein Structure Prediction and the Levinthal Paradox".

G. Opdenakker et al., GenBank, Accession Nos. X72308 & S57464, Jul. 25, 1994. Definition: "*H. sapiens* MCP-3 mRNA for monocyte chemotactic protein-3".

Sambrook, et al., Molecular Cloning: A Laboratory Manual, 2nd Ed., Chapters 9 and 11, CSHL: Cold Spring Harbor, New York, 1989.

Mikayama et al., Proc Natl Acad Sci U S A. Nov. 1, 1993;90(21)10056-60. "Molecular cloning and functional expression of a cDNA encoding glycosylation-inhibiting factor".

Voet et al., Biochemistry. John Wiley & Sons, Inc. pp. 126-128 and 228-234, (1990).

C. Auffray et al., Genbank Accession No. Z44443, Sep. 21, 1995. Definition: *H. sapiens* partial cDNA sequence; clone c-20f04.

US 8,343,492 B2

METHOD FOR BLOCKING BINDING OF CX3C CHEMOKINES USING CX3C CHEMOKINE ANTIBODIES

The present application is a divisional of U.S. patent application Ser. No. 12/833,069, filed Jul. 9, 2010; which is a continuation of U.S. patent application Ser. No. 12/510,586, filed Jul. 28, 2009; which is a continuation of U.S. patent application Ser. No. 12/198,626, filed Aug. 26, 2008; which is a continuation of U.S. patent application Ser. No. 11/495,801, filed Jul. 28, 2006; which is a continuation of U.S. patent application Ser. No. 10/397,559, filed Mar. 25, 2003; which is a division of U.S. patent application Ser. No. 09/771,023, filed Jan. 25, 2001, now U.S. Pat. No. 6,566,503; which is a division of U.S. patent application Ser. No. 09/093,482, filed Jun. 8, 1998; which is a division of U.S. patent application Ser. No. 08/786,068, filed Jan. 21, 1997; which is a continuation of U.S. patent application Ser. No. 08/649,006, filed May 16, 1996, now U.S. Pat. No. 6,548,654; which is a continuation of U.S. patent application Ser. No. 08/590,828 filed Jan. 24, 1996, each of which is incorporated herein by reference in its entirety.

FIELD OF THE INVENTION

The present invention contemplates compositions related to proteins which function in controlling development, differentiation, trafficking, and physiology of mammalian cells, e.g., cells of a mammalian immune system. In particular, it provides proteins which regulate or evidence development, differentiation, and function of various cell types, including hematopoietic cells.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.) (1993) *Fundamental Immunology* (3d ed.) Raven Press, N.Y.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which should lead to significant advancements in the diagnosis and therapy of numerous medical abnormalities, e.g., immune system and other disorders.

Lymphokines apparently mediate cellular activities in a variety of ways. They have been shown to support the proliferation, growth, and differentiation of pluripotential hematopoietic stem cells into vast numbers of progenitors comprising diverse cellular lineages making up a complex immune system. These interactions between cellular components are necessary for a healthy immune response. These different cellular lineages often respond in a different manner when lymphokines are administered in conjunction with other agents.

The chemokines are a large and diverse superfamily of proteins. The superfamily is subdivided into three branches, based upon whether the first two cysteines in the classical chemokine motif are adjacent (termed the "C—C" branch) or spaced by an intervening residue ("C—X—C"), or a new branch which lacks two cysteines in the corresponding motif, represented by the chemokines known as lymphotactins. See, e.g., Schall and Bacon (1994) *Current Opinion in Immunology* 6:865-873; and Bacon and Schall (1996) *Int. Arch. Allergy & Immunol.* 109:97-109.

Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modification of the effects of such factors. Thus, medical conditions where regulation of the development or physiology of relevant cells is inappropriate remain unmanageable.

SUMMARY OF THE INVENTION

The present invention reveals the existence of a previously unknown class of chemokine-motif containing molecules which are hereby designated the CX3C chemokines. The CX3Ckines have three amino acids which separate the cysteines in the corresponding region of the chemokine motif. Based on sequence analysis of the two CX3C protein sequences described below, it is apparent that the CX3Ckines do not belong to the C, C—C, or C—X—C chemokine families. They represent the first known members of a new heretofore unidentified class of chemokines designated CX3Ckines, or alternatively, the CX3C family of chemokines.

The present invention provides a composition of matter selected from an antibody binding site which specifically binds to a mammalian CX3C chemokine; an expression vector encoding a mammalian CX3C chemokine or fragment thereof; a substantially pure protein which is specifically recognized by the antibody binding site; and a substantially pure CX3C chemokine or peptide thereof, or a fusion protein comprising a 30 amino acid fragment of CX3C chemokine sequence.

In the antibody binding site embodiments, the antibody binding site may be: specifically immunoreactive with a mature protein selected from the group consisting of the polypeptides of SEQ ID NO: 2, 4, 6 and 8; raised against a purified or recombinantly produced human or mouse CX3C chemokine; in a monoclonal antibody, Fab, or F(ab)$_2$; immunoreactive with denatured antigen; or in a labeled antibody. In certain embodiments; the antibody binding site is detected in a biological sample by a method of: contacting a binding agent having an affinity for CX3C chemokine protein with the biological sample; incubating the binding agent with the biological sample to form a binding agent:CX3C chemokine protein complex; and detecting the complex. In a preferred embodiment, the biological sample is human, and the binding agent is an antibody.

A kit embodiment is provided possessing a composition, described above, with either instructional material for the use of the composition; or segregation of the composition into a container.

A nucleic acid embodiment of the invention includes an expression vector encoding a CX3C chemokine protein, wherein the protein specifically binds an antibody generated against an immunogen selected from the mature polypeptide portions of SEQ ID NO: 2, 4, 6, and 8. The vector may: encode a CX3C chemokine polypeptide with complete sequence identity to a naturally occurring human CX3C chemokine domain; encode a CX3C chemokine protein comprising sequence selected from the polypeptides of SEQ ID NO: 2, 4, 6, and 8; or comprise sequence selected from the nucleic acids of SEQ ID NO: 1, 3, 5, or 7. In other embodiments, the vector is capable of selectively hybridizing to a nucleic acid encoding a CX3C chemokine protein, e.g., a mature protein coding segment of SEQ ID NO: 1, 3, 5, or 7. In various preferred embodiments, the isolated nucleic acid is detected in a biological sample by a method: contacting a biological sample with a nucleic acid probe capable of selectively hybridizing to the nucleic acid; incubating the nucleic acid probe with the biological sample to form a hybrid of the nucleic acid probe with complementary nucleic acid sequences present in the biological sample; and determining the extent of hybridization of the nucleic acid probe to the complementary nucleic acid sequences. In such method, preferably the nucleic acid probe is capable of hybridizing to a nucleic acid encoding a protein consisting of the polypeptides of SEQ ID NO: 2, 4, 6, or 8

In protein embodiments, the isolated CX3C chemokine protein will preferably be of approximately 11,000 to 15,000 daltons when in unglycosylated form, and the CX3C chemokine protein specifically binds to an antibody generated against an immunogen; the polypeptides of SEQ ID NO: 2, 4, 6, or 8; and the CX3C chemokine lacks the cysteine structural motifs and sequence characteristic of a C, a CC, or a CXC chemokine. In various embodiments, the isolated CX3C chemokine protein is: selected from human CX3Ckine or mouse CX3Ckine; consists of a polypeptide comprising sequence from SEQ ID NO: 2, 4, 6, or 8; recombinantly produced, or a naturally occurring protein.

The present invention also embraces a cell transfected with the nucleic acid encoding a CX3C chemokine, e.g., where the nucleic acid has SEQ ID NO: 1, 3, 5, or 7.

The invention also provides a method of modulating physiology or development of a cell by contacting the cell with a CX3C chemokine, or an antagonist of the chemokine. In preferred embodiments, the physiology is attraction, and the cell is a peripheral blood monocyte or a T cell.

DETAILED DESCRIPTION

I. General

The present invention provides DNA sequences encoding mammalian proteins which exhibit structural properties or motifs characteristic of a cytokine or chemokine. For a review of the chemokine family, see, e.g., Lodi, et al. (1994) *Science* 263:1762-1767; Gronenborn and Clore (1991) *Protein Engineering* 4:263-269; Miller and Kranger (1992) *Proc. Nat'l Acad. Sci. USA* 89:2950-2954; Matsushima and Oppenheim (1989) *Cytokine* 1:2-13; Stoeckle and Baker (1990) *New Biol.* 2:313-323; Oppenheim, et al. (1991) *Ann. Rev. Immunol.* 9:617-648; Schall (1991) *Cytokine* 3:165-183; and *The Cytokine Handbook* Academic Press, NY. The proteins described herein are designated CX3Ckines because they were initially recognized as sharing significant structural features of chemokines, but whose structural features also exhibit sequence peculiarity, e.g., structural motifs, distinct from the other known branches of the chemokine molecules.

The best characterized embodiment of this family of proteins was discovered from a human and is designated human CX3C chemokine (GenBank Accession No. H14940). See, SEQ ID NO: 1-4 An additional CX3Ckine, represented by a mouse molecule, designated mouse CX3Ckine, is also described herein. See Table 1 and SEQ ID NO: 5-8. The descriptions below are directed, for exemplary purposes, to primate and rodent embodiments, e.g., human and mouse, but are likewise applicable to related embodiments from other, e.g., natural, sources. These sources should include various vertebrates, typically warm blooded animals, e.g., birds and mammals, particularly domestic animals, and primates.

In the human sequence (SEQ ID NO: 1-4), the signal sequence runs from about Met1 to Gly24, thus the mature polypeptide begins at about Gln25 and ends at about Val 397. A chemokine domain runs from about Gln25 to about Gly100; a stalk region, which possesses many potential glycosylation sites, runs from about Gly101 to about Gln341; a tranmembrane region begins at about Ala342 and ends at about Thr361; and an intracellular domain, containing two tyrosine phosphorylation sites at residues 382 and 392, runs from about Tyr362 to Val397.

TABLE 1

Mouse CX3C chemokine nucleic acid (SEQ ID NO: 7) and amino acid (SEQ ID NO: 8) sequences. The coding sequence runs from nucleotides 62-1249. The signal sequence runs from about Met1 through Gly24. The mature polypeptide runs from about Gln25 through Val395. The chemokine domain runs from about Gln25 through Gly100. The stalk region runs from about Gly101 through Gln339. The transmembrane domain runs from about Ala340 througn Phe358. The cytoplasmic domain runs from about Ala359 through Val395.

```
TGACTACTAG GAGCTGCGAC ACGGCCCAGC CTCCTGGCCG CCGAATTCCT GCACTCCAGC         60

C ATG GCT CCC TCG CCG CTC GCG TGG CTG CTG CGC CTG GCC GCG TTC           106
  Met Ala Pro Ser Pro Leu Ala Trp Leu Leu Arg Leu Ala Ala Phe
   1               5                  10                  15

TTC CAT TTG TGT ACT CTG CTG CCG GGT CAG CAC CTC GGC ATG ACG AAA       154
  Phe His Leu Cys Thr Leu Leu Pro Gly Gln His Leu Gly Met Thr Lys
                  20                  25                  30
```

TABLE 1-continued

Mouse CX3C chemokine nucleic acid (SEQ ID NO: 7) and amino acid (SEQ ID NO: 8) sequences. The coding sequence runs from nucleotides 62-1249. The signal sequence runs from about Met1 through Gly24. The mature polypeptide runs from about Gln25 through Val395. The chemokine domain runs from about Gln25 through Gly100. The stalk region runs from about Gly101 through Gln339. The transmembrane domain runs from about Ala340 througn Phe358. The cytoplasmic domain runs from about Ala359 through Val395.

| | |
|---|---|
| TGC GAA ATC ATG TGC GGC AAG ATG ACC TCA CGA ATC CCA GTG GCT TTG<br>Cys Glu Ile Met Cys Gly Lys Met Thr Ser Arg Ile Pro Val Ala Leu<br>                35                    40              45 | 202 |
| CTC ATC CGC TAT CAG CTA AAT CAG GAG TCC TGC GGC AAG CGT GCC ATT<br>Leu Ile Arg Tyr Gln Leu Asn Gln Glu Ser Cys Gly Lys Arg Ala Ile<br>        50                    55                    60 | 250 |
| GTC CTG GAG ACG ACA CAG CAC AGA CGC TTC TGT GCT GAC CCG AAG GAG<br>Val Leu Glu Thr Thr Gln His Arg Arg Phe Cys Ala Asp Pro Lys Glu<br>        65                    70                    75 | 298 |
| AAA TGG GTC CAA GAC GCC ATG AAG CAT CTG GAT CAC CAG GCT GCT GCC<br>Lys Trp Val Gln Asp Ala Met Lys His Leu Asp His Gln Ala Ala Ala<br> 80                  85                    90                    95 | 346 |
| CTC ACT AAA AAT GGT GGC AAG TTT GAG AAG CGG GTG GAC AAT GTG ACA<br>Leu Thr Lys Asn Gly Gly Lys Phe Glu Lys Arg Val Asp Asn Val Thr<br>                100                  105               110 | 394 |
| CCT GGG ATC ACC TTG GCC ACT AGG GGA CTG TCC CCA TCT GCC CTG ACA<br>Pro Gly Ile Thr Leu Ala Thr Arg Gly Leu Ser Pro Ser Ala Leu Thr<br>                115                  120               125 | 442 |
| AAG CCT GAA TCC GCC ACA TTG GAA GAC CTT GCT TTG GAA CTG ACT ACT<br>Lys Pro Glu Ser Ala Thr Leu Glu Asp Leu Ala Leu Glu Leu Thr Thr<br>                130                  135               140 | 490 |
| ATT TCC CAG GAG GCC AGG GGG ACC ATG GGG ACT TCC CAA GAG CCA CCG<br>Ile Ser Gln Glu Ala Arg Gly Thr Met Gly Thr Ser Gln Glu Pro Pro<br>                145                  150               155 | 538 |
| GCA GCA GTG ACC GGA TCA TCT CTC TCA ACT TCC GAG GCA CAG GAT GCA<br>Ala Ala Val Thr Gly Ser Ser Leu Ser Thr Ser Glu Ala Gln Asp Ala<br>160                    165                  170               175 | 586 |
| GGG CTT ACG GCT AAG CCT CAG AGC ATT GGA AGT TTT GAG GCG GCT GAC<br>Gly Leu Thr Ala Lys Pro Gln Ser Ile Gly Ser Phe Glu Ala Ala Asp<br>                180                  185               190 | 634 |
| ATC TCC ACC ACC GTT TGG CCG AGT CCT GCT GTC TAC CAA TCT GGA TCT<br>Ile Ser Thr Thr Val Trp Pro Ser Pro Ala Val Tyr Gln Ser Gly Ser<br>                195                  200               205 | 682 |
| AGC TCC TGG GCT GAG GAA AAA GCT ACT GAG TCC CCC TCC ACT ACA GCC<br>Ser Ser Trp Ala Glu Glu Lys Ala Thr Glu Ser Pro Ser Thr Thr Ala<br>                210                  215               220 | 730 |
| CCA TCT CCT CAG GTG TCC ACT ACT TCA CCT TCA ACC CCA GAG GAA AAT<br>Pro Ser Pro Gln Val Ser Thr Thr Ser Pro Ser Thr Pro Glu Glu Asn<br>                225                  230               235 | 778 |
| GTT GGG TCC GAA GGC CAA CCC CCA TGG GTC CAG GGA CAG GAC CTC AGT<br>Val Gly Ser Glu Gly Gln Pro Pro Trp Val Gln Gly Gln Asp Leu Ser<br>240                    245                  250               255 | 826 |
| CCA GAG AAG TCT CTA GGG TCT GAG GAG ATA AAC CCA GTT CAT ACT GAT<br>Pro Glu Lys Ser Leu Gly Ser Glu Glu Ile Asn Pro Val His Thr Asp<br>                260                  265               270 | 874 |
| AAT TTC CAG GAG AGG GGG CCT GGC AAC ACA GTC CAC CCC TCA GTG GCT<br>Asn Phe Gln Glu Arg Gly Pro Gly Asn Thr Val His Pro Ser Val Ala<br>                275                  280               285 | 922 |
| CCC ATC TCC TCT GAA GAG ACC CCC AGC CCA GAG CTG GTG GCC TCG GGC<br>Pro Ile Ser Ser Glu Glu Thr Pro Ser Pro Glu Leu Val Ala Ser Gly<br>                290                  295               300 | 970 |
| AGC CAG GCT CCT AAG ATA GAG GAA CCC ATC CAT GCC ACT GCA GAT CCC<br>Ser Gln Ala Pro Lys Ile Glu Glu Pro Ile His Ala Thr Ala Asp Pro | 1018 |

TABLE 1-continued

Mouse CX3C chemokine nucleic acid (SEQ ID NO: 7) and amino acid (SEQ ID NO: 8) sequences. The coding sequence runs from nucleotides 62-1249. The signal sequence runs from about Met1 through Gly24. The mature polypeptide runs from about Gln25 through Val395. The chemokine domain runs from about Gln25 through Gly100. The stalk region runs from about Gly101 through Gln339. The transmembrane domain runs from about Ala340 througn Phe358. The cytoplasmic domain runs from about Ala359 through Val395.

```
              305                 310                 315
CAG AAA CTG AGT GTG CTT ATC ACT CCT GTC CCC GAC ACC CAG GCA GCC          1066
Gln Lys Leu Ser Val Leu Ile Thr Pro Val Pro Asp Thr Gln Ala Ala
320                 325                 330                 335

ACA AGG AGG CAG GCA GTG GGG CTA CTG GCT TTC CTT GGT CTT CTT TTC          1114
Thr Arg Arg Gln Ala Val Gly Leu Leu Ala Phe Leu Gly Leu Leu Phe
                340                 345                 350

TGC CTA GGG GTG GCC ATG TTT GCT TAC CAG AGC CTT CAG GGC TGT CCC          1162
Cys Leu Gly Val Ala Met Phe Ala Tyr Gln Ser Leu Gln Gly Cys Pro
            355                 360                 365

CGC AAA ATG GCG GGG GAA ATG GTA GAA GGC CTC CGC TAC GTC CCC CGT          1210
Arg Lys Met Ala Gly Glu Met Val Glu Gly Leu Arg Tyr Val Pro Arg
        370                 375                 380

AGC TGT GGC AGT AAC TCA TAC GTC CTG GTG CCA GTG TGA GCTGCTTGCC           1259
Ser Cys Gly Ser Asn Ser Tyr Val Leu Val Pro Val *
    385                 390                 395

TGCCTGCCTG TGTCCAGAGT GTGATTCGGA CAGCTGTCTG GGACCCCCC CCCATCCTCA         1319

TACCCACCTT CATCCACGCT GGGGAAATGG GAATGGAGAA GCTGGACCTC CAGGGGCTGT        1379

GGGCTCCATC CAATCCCCCT TCCCCCGAGG GGTGGCCCCG GAGGCCACCC TAGACCACTA        1439

TTCACTTATC AGAGACAGAG CAGGTGACCT TCCAGCTCCT CTATATTTGA AAGAATCCTC        1499

TGCTGCTGGC TGGTTAGAGG GGCCCTTGAC ACCCCAACTC CAGTGAACAA TTATTTATTG        1559

GATTCCCAGC CCCTGCGACG ACACCTGTTT CCCGCGCGCA CCGTGGTCCG CCCATATCAC        1619

AAGCAGCAGG CCAGGCCTAT CTGCCTGTCC CCCTGACCTC CTTGTGTCTC CTGGCTTTGC        1679

TGCAGTCGCC AGCCCTTCTC CTCCCCGGCC AGCCGCGGTG CTATCTGCCC TATGTCTCCC       1739

TCTATCCCCT GTACAGAGCG CACCACCATC ACCATCAACA CCGCTGTTGT GTCTTTTCTT       1799

GCATGAGGTT AAAGCTGTGT TTTCTGGAGC TCTCCGGGAA GGGAGACAAG CTTGCGAGAG       1859

GGTTTAAAGT GTTCCTCCCC AGACTTGGAT GTGCTGTGAG GCATGCTGC GTCTGAAGGA        1919

AGGGTCCAGT CCCCACTCGG CTACCAGCAC ACAAAGTGC CCCACCTGTA AAAGGAAAGA        1979

AACGTGGTCC AGAGCTGGCA ATAACCTATG GCCCTGACAT CATCACTTTC TCTGAGATCC       2039

TTGTCTCCAC CCCTGGGTGC AACCCCACCC CTTATCAACA TTAATAGTCA CTGCCATTCC       2099

ACTGGACTGA CATTTTTGTA CCCTGTGATT CTGAGGGCTG GCAAGGAGTG GCTTGAGAGT       2159

GCAGATCGTA CCCTGTATGC CCCCCCCAAA TGGAGGCTGA GTTGGGGACT GCAGGAACA        2219

GAGGCCAACT CAGATGGCTT CCCCTGTGTT CTCACTAGAA ACCCCTCCCC CATGCACCAA       2279

GGTGACAGTC ACAGGTCTGC CCTGGCTAAA GGACAAGCCA CATAGGAAAG ATTAGGACAA       2339

GCCCCTCGGA GGCAGAGGAT CCAGGGTAAA CCCCTGGAGT GGCCACAAAC CCAATTTCAG       2399

TGTAGGGACT TGTGCATGTG TGTACTTGCA TAGTCAGACA GAGGCTGCCA GGGTCCTTTC       2459

CTGTCTCTGA GAGCAGTGTT CACGCCAAGG ACTCACCTTT GCCCCATTG CAGGCAGGGC        2519

CAGAACTCCC ATAGCATTCT CCAAGAGCCC TGTGACATTT TCTGGAAGGA ACTCTGCCCT       2579

GGGCGCAAAG TGACTGCTGA AGCAAGGAGC AGCTGAGCAG CACCCAGCG GAGCTGAGCC        2639

GGCAGGCCAC GCCCCTCGGG GGGGGGCATT TCTACCCGCC CTGCTCTGAA TAGCTCCAAC       2699
```

TABLE 1-continued

Mouse CX3C chemokine nucleic acid (SEQ ID NO: 7) and amino acid (SEQ ID NO: 8) sequences. The coding sequence runs from nucleotides 62-1249. The signal sequence runs from about Met1 through Gly24. The mature polypeptide runs from about Gln25 through Val395. The chemokine domain runs from about Gln25 through Gly100. The stalk region runs from about Gly101 through Gln339. The transmembrane domain runs from about Ala340 throuogn Phe358. The cytoplasmic domain runs from about Ala359 through Val395.

```
TTCACCTTAG GAGCCTCCCA GGGGCGAGCT TCACCCAGAA GCCAGTGACT CACTCCTTGA    2759

TTGGTGGAAG CTCAGTTGGC TCCTGAGAGT GAGGAAGCCA ACCCTTTGTC GACCCTCCTC    2819

CTGGGAAGCC TGTGGGCGGC TCTGATCATG CTCCACAGAA CCAGTTGTAG GCCTGAGCCG    2879

CAGCAGCCCG AGTGCACTAT ATCCTGGCTC CTTCGGTGGG GAACCTTTAA GGGTTGGGAC    2939

ACCCGTCATC GGACTTTGTT GGTTCCTCCC TCCCAGAGCA GAATGTGGGC CGTAACAATC    2999

TGAGGAGGAC TTTAAAAGTT GTTGATCCTT TAGGGTTTTT TTTCAAGCAT CATTACCAAT    3059

GTCTGT                                                                3065
```

The CX3Ckine proteins of this invention are defined in part by their physicochemical and biological properties. The biological properties of the human and mouse CX3Ckines described herein, e.g., human CX3Ckine and mouse CX3Ckine, are defined by their amino acid sequence, and mature size. They also should share biological properties. The human and mouse CX3Ckine molecules exhibit about 70-80% amino acid identity, depending on whether the signal or mature sequences are compared. One of skill will readily recognize that some sequence variations may be tolerated, e.g., conservative substitutions or positions remote from the helical structures, without altering significantly the biological activity of the molecule.

Table 2 shows a sequence alignment of human CX3Ckine amino acid sequence (CX3C) with the C—X—C chemokine Groa (Gro), the C chemokine lymphotactin (LTn), and the C—C chemokine Macrophage inflammatory protein 1β (MIP-1β).

TABLE 2

Comparison of various chemokines

Exon 1

| | |
|---|---|
| Gro (SEQ ID NO: 9) | MIPATRSLLCAALLLLATSRLATG |
| LTn (SEQ ID NO: 10) | MRLLLLTFLGVCCLTPWVV |
| MIP-1β (SEQ ID NO: 11) | MKLCVSALSLLLLVAAFCAPGFS |
| CX3 (SEQ ID NO: 2) | MAPISLSWLLRLATFCHLTVLLAG |

Exon 2

| | |
|---|---|
| Gro | APIANELRCQCLQTMA.GIHLKNIQSLKVLPSGPHCTQT |
| LTn | EGVGTEVLEESSCVNLQTQRLPVQKIKTYIIWEG....AMR |
| MIP | APMGSDPPTSCCFSYTARKLPRNFVVDYYETSSL..CSQP |
| CX3 | QHHGVTKCNITC.SKMTSKIPVALLIHYQQNQAS..CGKR |

Exon 3

| | |
|---|---|
| GRO | EVIATLKNGREACLDPEAPLVQKIVQKMLKGVPK |
| LTN | AVIFVTKRGLKICADPEAKWVLAAIKTVDGRASTRKNMAETVPGTGAQRSTSTAITLTG |
| MIP | AVVFQTKRSKQVCADPSESWVQEYVYDLELN |
| CX3 | AIILETRQHRLFCADPKEQWVKDAMQHLDRQAAALTRNG . . . |

CX3Ckines are present in specific tissue types, e.g., neural tissues, and the interaction of the protein with a receptor will be important for mediating various aspects of cellular physiology or development. The cellular types which express message encoding CX3Ckines suggest that signals important in cell differentiation and development are mediated by them. See, e.g., Gilbert (1991) *Developmental Biology* (3d ed.) Sinauer Associates, Sunderland, MA; Browder, et al. (1991) *Developmental Biology* (3d ed.) Saunders, Philadelphia, Pa.; Russo, et al. (1992) *Development: The Molecular Genetic Approach* Springer-Verlag, New York, N.Y.; and Wilkins (1993) *Genetic Analysis of Animal Development* (2d ed.) Wiley-Liss, New York, N.Y. Moreover, CX3Ckine expression should serve to define certain cell subpopulations.

The CX3C chemokine producing profile of various cells is elucidated herein. Screening a cDNA library generated from brain provided a novel cytokine, designated human CX3Ckine. Human CX3Ckine exhibits distant similarity to members of the C, C—C, and C—X—C chemokine families, with another heretofore unrecognized number of amino acid residues separating the characteristic cysteines in the motif which is peculiar to and partially defines chemokines. These observations suggest that the CX3Ckines represent novel additions to the chemokine superfamily.

CX3C chemokine protein biochemistry was assessed in mammalian expression systems. Human embryonic kidney 293 cells (HEK 293) transfected with a mammalian expression construct encoding full-length CX3C chemokine were metabolically labeled with $^{35}S$ cysteine and methionine. CX3C chemokine was produced as a protein of Mr ~95 kDa; control transfected supernatants contained no such species. Neuraminidase and glycosidases reduced the Mr of CX3C chemokine from ~95 kDa to ~45 kDa, suggesting that the recombinant form, is glycosylated substantially. CX3C chemokine cDNA, encoding a predicted membrane-bound protein, encodes a glycoprotein which is released from cells by an undefined mechanism.

The pro-migratory activities of CX3C chemokine have been assessed in microchemotaxis assays. CX3C chemokine appears to be a potent attractant of peripheral blood monocytes and T cells. Pro-migratory activity for blood neutrophils has been difficult to demonstrate.

The CX3C chemokine gene has been mapped to human chromosome 16. Mapping studies also indicate the possibility of a pseudogene or related gene on human chromosome 14. Sequencing of genomic DNA fragments suggests CX3C chemokine gene has an intron which begins near or in the codon encoding Ile 64. Other intron/exon boundaries have yet to be mapped, but such will be easily accomplished by standard methods.

The membrane bound form of CX3Ckine possesses proadherent properties for circulating T cells and monocytes. A secreted or soluble form, consisting of the chemokine domain and the stalk region, is able to inhibit this proadhesive activity. This suggests that the membrane bound form of CX3Ckine may be a potent regulator of circulating leukocytes, and thus may be involved in various inflammatory diseases, e.g., arthritis. The soluble form may be used as a regulator of proadherence, especially in conditions of compromised immune response.

CX3C chemokine's properties as a T cell and monocyte chemoattractant, coupled with its distribution in brain and other organs, suggests that CX3C chemokine may be involved in the pathogenesis of such CNS inflammatory disorders as multiple sclerosis, and other pathologies involving neurogenic inflammation. Since CX3C chemokine distribution is not limited to the brain, however, the entire spectrum of inflammatory, infectious, and immunoregulatory states thought to involve other chemokines must also now be considered for CX3C chemokine. See, e.g., Frank, Et al. (eds.) (1995) *Samter's Immunologic Diseases* 5th ed., vols. I and II, Little, Brown, and Co., Boston, Mass.

II. Definitions

The term "binding composition" refers to molecules that bind with specificity to a CX3Ckine, e.g., in an antibody-antigen interaction. However, other compounds, e.g., receptor proteins, may also specifically associate with CX3Ckines to the exclusion of other molecules. Typically, the association will be in a natural physiologically relevant protein-protein interaction, either covalent or non-covalent, and may include members of a multiprotein complex, including carrier compounds or dimerization partners. The molecule may be a polymer, or chemical reagent. No implication as to whether a CX3Ckine is either the ligand or the receptor of a ligand-receptor interaction is necessarily represented, other than whether the interaction exhibits similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.) Pergamon Press, Tarrytown, N.Y.

The term "binding agent:CX3Ckine protein complex", as used herein, refers to a complex of a binding agent and a CX3Ckine protein that is formed by specific binding of the binding agent to the CX3Ckine protein, e.g., preferably the chemokine domain. Specific binding of the binding agent means that the binding agent has a specific binding site that recognizes a site on the CX3Ckine protein. For example, antibodies raised to a CX3Ckine protein and recognizing an epitope on the CX3Ckine protein are capable of forming a binding agent:CX3Ckine protein complex by specific binding. Typically, the formation of a binding agent:CX3Ckine protein complex allows the measurement of CX3Ckine protein in a mixture of other proteins and biologics. The term "antibody:CX3Ckine protein complex" refers to an embodiment in which the binding agent is an antibody. The antibody may be monoclonal, polyclonal, or a binding fragment of an antibody, e.g, an Fab of F(ab)$_2$ fragment. The antibody will preferably be a polyclonal antibody for cross-reactivity purposes.

"Homologous" nucleic acid sequences, when compared, exhibit significant similarity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

As used herein, the term "CX3Ckine protein" shall encompass, when used in a protein context, a protein having amino acid sequences, particularly from the chemokine motif portions, shown in SEQ ID NO: 2, 4, 6, or 8, or a significant fragment of such a protein, e.g., preferably the chemokine domain. The invention also embraces a polypeptide which exhibits similar structure to human or mouse CX3Ckine, e.g., which interacts with CX3Ckine specific binding components. These binding components, e.g., antibodies, typically bind to a CX3Ckine with high affinity, e.g., at least about 100 nM, usually better than about 30 nM, preferably better than about 10 nM, and more preferably at better than about 3 nM.

The term "polypeptide" or "protein" as used herein includes a significant fragment or segment of chemokine motif portion of a CX3Ckine, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, etc.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants. Mutation of protease cleavage sites may also be accomplished.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1-3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be evaluated in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl)dimethyl-ammonio]-1-propane sulfonate), or a low enough concentration as to avoid significant disruption of structural or physiological properties of the protein.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1, 3, 5 or 7. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) *Nuc. Acids Res.* 12:203-213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. See, e.g., Wetmur and Davidson (1968) *J. Mol. Biol.* 31:349-370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

CX3Ckines from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human CX3Ckine protein immunogen with the amino acid sequence depicted in SEQ ID NO: 2, 4, 6, or 8 can be selected to obtain antibodies specifically immunoreactive with CX3Ckine proteins and not with other proteins. These antibodies recognize proteins highly similar to the homologous mouse CX3Ckine protein.

III. Nucleic Acids

Human CX3Ckine is exemplary of a larger class of structurally and functionally related proteins. These soluble chemokine proteins will serve to transmit signals between different cell types. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, dog, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides. Moreover, reverse translation using the redundancy in the genetic code may provide synthetic genes which may encode essentially identical proteins often with a condo usage selection preferred for expression in a given host cell.

Techniques for nucleic acid manipulation of genes encoding CX3Ckine proteins, such as subcloning nucleic acid sequences encoding polypeptides into expression vectors, labelling probes, DNA hybridization, and the like are described generally in Sambrook, et al. (1989) *Molecular Cloning: A Laboratory Manual* (2nd ed.) Vol. 1-3, Cold Spring Harbor Laboratory, Cold Spring Harbor Press, NY, which is incorporated herein by reference. This manual is hereinafter referred to as "Sambrook, et al."

There are various methods of isolating DNA sequences encoding CX3Ckine proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding CX3Ckine proteins, or primers can be designed, e.g., using flanking sequence, for use in amplification techniques such as PCR, for the isolation of DNA encoding CX3Ckine proteins.

To prepare a cDNA library, mRNA is isolated from cells which express a CX3Ckine protein. cDNA is prepared from the mRNA and ligated into a recombinant vector. The vector is transfected into a recombinant host for propagation, screening, and cloning. Methods for making and screening cDNA libraries are well known. See Gubler and Hoffman (1983) *Gene* 25:263-269 and Sambrook, et al.

For a genomic library, the DNA can be extracted from tissue and either mechanically sheared or enzymatically digested to yield fragments, e.g., of about 12-20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180-182. Colony hybridization is carried out as generally described in e.g., Grunstein, et al. (1975) *Proc. Natl. Acad. Sci. USA.* 72:3961-3965.

DNA encoding a CX3Ckine protein can be identified in either cDNA or genomic libraries by its ability to hybridize with the nucleic acid probes described herein, e.g., in colony or plaque hybridization assays. The corresponding DNA regions are isolated by standard methods familiar to those of skill in the art. See, e.g., Sambrook, et al. Alternatively, sequence databases, e.g., GenBank, may be evaluated for similar or corresponding sequences.

Various methods of amplifying target sequences, such as the polymerase chain reaction, can also be used to prepare DNA encoding CX3Ckine proteins. Polymerase chain reaction (PCR) technology is used to amplify such nucleic acid sequences directly from mRNA, from cDNA, and from genomic libraries or cDNA libraries. The isolated sequences encoding CX3Ckine proteins may also be used as templates for PCR amplification.

Typically, in PCR techniques, oligonucleotide primers complementary to two 5' regions in two strands of the DNA region to be amplified are synthesized. The polymerase chain reaction is then carried out using the two opposite primers. See Innis, et al. (eds.) (1990) *PCR Protocols: A Guide to Methods and Applications* Academic Press, San Diego, Calif. Primers can be selected to amplify the entire regions encoding a full-length CX3Ckine protein or to amplify smaller DNA segments as desired. Once such regions are PCR-amplified, they can be sequenced and oligonucleotide probes can be prepared from sequence obtained using standard techniques. These probes can then be used to isolate DNA's encoding CX3Ckine proteins.

Oligonucleotides for use as probes are usually chemically synthesized according to the solid phase phosphoramidite triester method first described by Beaucage and Carruthers (1983) *Tetrahedron Lett.* 22(20):1859-1862, or using an automated synthesizer, as described in Needham-VanDevanter, et al. (1984) *Nucleic Acids Res.* 12:6159-6168. Purification of oligonucleotides is performed, e.g., by native acrylamide gel electrophoresis or by anion-exchange HPLC as described in Pearson and Regnier (1983) *J. Chrom.* 255:137-149. The sequence of the synthetic oligonucleotide can be verified using, e.g., the chemical degradation method of Maxam, A. M. and Gilbert, W. in Grossman, L. and Moldave (eds.) (1980) *Methods in Enzymology* 65:499-560 Academic Press, New York.

An isolated nucleic acid encoding a human CX3Ckine protein was identified. The nucleotide sequence and corresponding open reading frame are provided in SEQ ID NO: 1 and 2; with further sequences provided in SEQ ID NO: 3 and 4. Correspondingly, a mouse sequence was identified and its nucleotide and corresponding open reading frame are provided as SEQ ID NO: 5-8.

These CX3Ckines exhibit limited similarity to portions of chemokines, particularly the chemokine domains. See, e.g., Matsushima and Oppenheim (1989) *Cytokine* 1:2-13; Oppenheim, et al. (1991) *Ann. Rev. Immunol.* 9:617-648; Schall (1991) *Cytokine* 3:165-183; and Gronenborn and Clore (1991) *Protein Engineering* 4:263-269. In particular, the human CX3Ckine shows similarity to the C class of chemokines in the carboxyl-terminal portion, particularly with respect to length, and at the positions corresponding, in the numbering of mature human sequence, to the cys-ala-asp-pro sequence at positions 50-53; and the trp-val at positions 57-58. CX3Ckines have a much longer carboxyl terminal tail than the members of the CC or CXC chemokine families, and this "stalk" region may play a role in chemokine presentation. Notably, the spacing of conserved cysteine residues in the CXC and CC families of chemokines are absent in the human CX3Ckine embodiment. Other features of comparison are apparent between the CX3Ckine and chemokine families. See, e.g., Lodi, et al. (1994) *Science* 263:1762-1766. In particular, β-sheet and α-helix residues can be determined using, e.g., RASMOL program, see Sayle and Milner-White (1995) *TIBS* 20:374-376; or Gronenberg, et al. (1991) *Protein Engineering* 4:263-269; and other structural features are defined in Lodi, et al. (1994) *Science* 263:1762-1767. These secondary and tertiary features assist in defining further the C, CC, and CXC structural features, along with spacing of appropriate cysteine residues.

Based upon the structural modeling and insights in the binding regions of the chemokines, it is predicted that residues in the mature human protein, lacking a signal of 24 residues, 26 (his), 28 (gln), 40 (ile), 42 (glu), 47 (arg) and 48 (leu) should be important for chemokine binding to cells. Residues at the amino terminus are probably not involved in receptor binding or specificity.

Moreover, exon boundaries are predicted to correspond to protein segments including the signal sequence through about the second residue (his) in the mature protein; from there to about three residues past the third cys (around the arg-ala); and from there to the end. The third exon appears to exhibit relatively high similarity to the other chemokines. The second exon would probably be most characteristic of the CX3C chemokines, and would be the preferred segment to use to search for homology in other variants, e.g, species or otherwise. In particular, segments expected to be preferred in producing CX3C chemokine specific antibodies will include peptides or sequence in the region from the second residue of the mature protein (his) through about the third residue after the third cysteine (arg). Fragments of at least about 8-10 residues in that region would be especially interesting peptides, e.g., starting at residue positions of the mature 1, 2, 3, etc. Those fragments would typically end in that region, e.g., at residue 37, 36, 35, etc. Other interesting peptides of various lengths would include ones which begin or end in other positions of the protein, e.g., at residues 87, 86, etc., with lengths ranging, e.g., from about 8 to 20, 25, 30, 35, 40, etc. Corresponding fragments of other mammalian CX3Ckine, e.g., mouse, will be preferred embodiments.

This invention provides isolated DNA or fragments to encode a CX3Ckine protein. In addition, this invention provides isolated or recombinant DNA which encodes a protein or polypeptide which is capable of hybridizing under appropriate conditions, e.g., high stringency, with the DNA sequences described herein. Said biologically active protein or polypeptide can be an intact ligand, or fragment, and have an amino acid sequence as disclosed in SEQ ID NO: 2, 4, 6, or 8. Preferred embodiments will be full length natural sequences, from isolates, e.g., about 11,000 to 12,500 daltons in size when unglycosylated, or fragments of at least about 6,000 daltons, more preferably at least about 8,000 daltons. In glycosylated form, the protein may exceed 12,500 daltons. Further, this invention contemplates the use of isolated or recombinant DNA, or fragments thereof, which encode proteins which are homologous to a CX3Ckine protein or which were isolated using cDNA encoding a CX3Ckine protein as a probe. The isolated DNA can have the respective regulatory sequences in the 5' and 3' flanks, e.g., promoters, enhancers, poly-A addition signals, and others.

IV. Making CX3Ckines

DNAs which encode a CX3Ckine or fragments thereof can be obtained by chemical synthesis, screening cDNA libraries, or by screening genomic libraries prepared from a wide variety of cell lines or tissue samples. The redundancy of the genetic code provides a number of polynucleotide sequences which should encode the same protein.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each CX3Ckine or its fragments, e.g., the chemokine domain, can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., CX3Ckine, or portions thereof, may be expressed as fusions with other proteins or possessing an epitope tag. Such is applicable also to antigen binding sites.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention encompass DNAs which encode a CX3Ckine, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a CX3Ckine protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a CX3Ckine gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express CX3Ckines or CX3Ckine fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) *Vectors: A Survey of Molecular Cloning Vectors and Their Uses* 10:205-236 Buttersworth, Boston, Mass.

Lower eukaryotes, e.g., yeasts and *Dictyostelium*, may be transformed with CX3Ckine sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are typically the preferred host cells for expression of the functionally active CX3Ckine protein. In principle, many higher eukaryotic tissue culture cell lines may be used, e.g., insect baculovirus expression systems, whether from an invertebrate or vertebrate source. However, mammalian cells are preferred to achieve proper processing, both cotranslationally and post-translationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell. Biol.* 5:1136-1142; pMC1neo Poly-A, see Thomas, et al. (1987) *Cell* 51:503-512; and a baculovirus vector such as pAC 373 or pAC 610.

It is likely that CX3Ckines need not be glycosylated to elicit biological responses. However, it will occasionally be desirable to express a CX3Ckine polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, the CX3Ckine gene may be co-transformed with one or more genes encoding mammalian or other glycosylating enzymes. It is further understood that over glycosylation may be detrimental to CX3Ckine biological activity, and that one of skill may perform routine testing to optimize the degree of glycosylation which confers optimal biological activity.

A CX3Ckine, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427-454; Tse, et al. (1985) *Science* 230:1003-1008; and Brunner, et al. (1991) *J. Cell Biol.* 114:1275-1283.

Now that CX3Ckines have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The CX3Ckines of this invention can be obtained in varying degrees of purity depending upon its desired use. Purification can be accomplished by use of known protein purification techniques or by the use of the antibodies or binding partners herein described, e.g., in immunoabsorbant affinity chromatography. See, e.g., Coligan, et al. (eds.) (1995 and periodic supplements) *Current Protocols in Protein Science*, John Wiley and Sons, New York, N.Y. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the CX3Ckines as a result of recombinant DNA techniques, see below.

Multiple cell lines may be screened for one which expresses a CX3Ckine at a high level compared with other cells. Various cell lines, e.g., a mouse thymic stromal cell line TA4, is screened and selected for its favorable handling properties. Natural CX3Ckines can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or $His_6$ segments, can be used for such purification features.

V. Antibodies

Antibodies can be raised to various CX3Ckines, including individual, polymorphic, allelic, strain, or species variants, and fragments thereof, both in their naturally occurring (full-length) forms and in their recombinant forms. Additionally, antibodies can be raised to CX3Ckines in either their active or native forms or in their inactive or denatured forms. Anti-idiotypic antibodies may also be used.

A. Antibody Production

A number of immunogens may be used to produce antibodies specifically reactive with CX3Ckine proteins. Recombinant protein is a preferred immunogen for the production of monoclonal or polyclonal antibodies. Naturally occurring protein may also be used either in pure or impure form. Synthetic peptides, made using the human or mouse CX3Ckine protein sequences described herein, may also used as an immunogen for the production of antibodies to CX3Ckines, e.g., the chemokine domains thereof. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated for subsequent use in immunoassays to measure the protein.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the CX3Ckine protein or fragment of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511-519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275-1281.

Antibodies, including binding fragments and single chain versions, against predetermined fragments of CX3Ckines can be raised by immunization of animals with conjugates of the fragments with carrier proteins as described above. Monoclonal antibodies are prepared from cells secreting the desired antibody. These antibodies can be screened for binding to normal or defective CX3Ckines, or screened for agonistic or antagonistic activity, e.g., mediated through a receptor. These monoclonal antibodies will usually bind with at least a $K_D$ of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246: 1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or noncovalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029-10033.

The antibodies of this invention are useful for affinity chromatography in isolating CX3Ckine protein. Columns can be prepared where the antibodies are linked to a solid support, e.g., particles, such as agarose, SEPHADEX, or the like, where a cell lysate or supernatant may be passed through the column, the column washed, followed by increasing concentrations of a mild denaturant, whereby purified CX3Ckine protein will be released.

The antibodies may also be used to screen expression libraries for particular expression products. Usually the antibodies used in such a procedure will be labeled with a moiety allowing easy detection of presence of antigen by antibody binding.

Antibodies to CX3Ckines may be used for the identification of cell populations expressing CX3Ckines. By assaying the expression products of cells expressing CX3Ckines it is possible to diagnose disease, e.g., immune-compromised conditions.

Antibodies raised against each CX3Ckine will also be useful to raise anti-idiotypic antibodies. These will be useful in detecting or diagnosing various immunological conditions related to expression of the respective antigens.

B. Immunoassays

A particular protein can be measured by a variety of immunoassay methods. For a review of immunological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of CX3Ckine proteins can be performed by a variety of methods known to those skilled in the art. In brief, immunoassays to measure the protein can be competitive or noncompetitive binding assays. In competitive binding assays, the sample to be analyzed competes with a labeled analyte for specific binding sites on a capture agent bound to a solid surface. Preferably the capture agent is an antibody specifically reactive with CX3Ckine proteins produced as described above. The concentration of labeled analyte bound to the capture agent is inversely proportional to the amount of free analyte present in the sample.

In a competitive binding immunoassay, the CX3Ckine protein present in the sample competes with labeled protein for binding to a specific binding agent, for example, an antibody specifically reactive with the CX3Ckine protein. The binding agent may be bound to a solid surface to effect separation of bound labeled protein from the unbound labeled protein. Alternatively, the competitive binding assay may be conducted in liquid phase and a variety of techniques known in the art may be used to separate the bound labelled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

CX3Ckine proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labelled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of CX3Ckine proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above employ labeled assay components. The label may be coupled directly or indirectly to the desired component of the assay according to methods well known in the art. A wide variety of labels and methods may be used. Traditionally, a radioactive label incorporating $^3H$, $^{125}I$, $^{35}S$, $^{14}C$, or $^{32}P$ was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

In brief, immunoassays to measure antisera reactive with CX3Ckine proteins can be competitive or noncompetitive binding assays. In competitive binding assays, the sample analyte competes with a labeled analyte for specific binding sites on a capture agent bound to a solid surface. Preferably the capture agent is a purified recombinant CX3Ckine protein produced as described above. Other sources of CX3Ckine proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labelled binding agent can be used. A variety of different immunoassay formats, separation techniques, and labels can be also be used similar to those described above for the measurement of CX3Ckine proteins.

VI. Purified CX3Ckines

Human CX3Ckine amino acid sequences are provided in SEQ ID NO: 2 and 4. Mouse nucleotide and amino acid sequences are provided in SEQ ID NO: 5, 6, 7, and 8.

Purified protein or defined peptides are useful for generating antibodies by standard methods, as described above. Synthetic peptides or purified protein, e.g., the chemokine domains, can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference. Alternatively, a CX3Ckine receptor can be useful as a specific binding reagent, and advantage can be taken of its specificity of binding, for, e.g., purification of a CX3Ckine ligand.

The specific binding composition can be used for screening an expression library made from a cell line which expresses a CX3Ckine. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic an polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) *Science* 266:776-779. Since CX3Ckines appear to be soluble proteins, the gene will normally possess an N-terminal signal sequence, which is removed upon processing and secretion, and the putative cleavage site is between amino acids 24 (gly) and 25 (gin) in SEQ ID NO: 2 or 4, though it may be slightly in either direction. Analysis of the structural features in comparison with the most closely related reported sequences has revealed similarities with other cytokines, particularly the class of proteins known as chemokines. Within the chemokines are two subgroups, the CC and CXC subgroups. The CX3Ckine family shares various features with each of these groups, but its combination of features is distinctive and defines a new family of related chemokines.

While further structural features result from the sequences provided in SEQ ID NO: 1 through 8, the "chemokine on a stick" feature is provided through the stalk region which possesses many sites which may provide a heavily glycosylated domain. The stalk structure may be important in CX3C chemokine presentation to other cells. In fact, it appears that the stalk region may be processed to release the soluble chemokine. This suggests the possibility of substituting the CX3C chemokine domain with other chemokines to effect efficient presentation to appropriate target cells.

In addition, the "stalk" regions are likely to affect solubility and pharmacological aspects of the protein. As such, this region will be the target of analysis to evaluate and modulate such features as pharmacokinetics. Truncation of that portion may affect half-life, clearance, and accessibility of the chemokine domains.

VII. Physical Variants

This invention also encompasses proteins or peptides having substantial amino acid sequence similarity with an amino acid sequence of a CX3Ckine. Natural variants include individual, polymorphic, allelic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50-100% similarity (if gaps can be introduced), to 75-100% similarity (if conservative substitutions are included) with the amino acid sequence of the CX3Ckine. Similarity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443-453; Sankoff, et al. (1983) *Time Warps, String Edits, and Macromolecules: The Theory and Practice of Sequence Comparison* Chapter One, Addison-Wesley, Reading, Mass.; and software packages from Intelli-Genetics, Mountain View, Calif.; and the University of Wisconsin Genetics Computer Group, Madison, Wis.

Nucleic acids encoding mammalian CX3Ckine proteins will typically hybridize to the nucleic acid sequence of SEQ ID NO: 1, 3, 5 or 7 under stringent conditions. For example, nucleic acids encoding human CX3Ckine proteins will normally hybridize to the nucleic acid of SEQ ID NO: 1 under stringent hybridization conditions. Generally, stringent conditions are selected to be about 10° C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C.

An isolated CX3Ckine DNA can be readily modified by nucleotide substitutions, nucleotide deletions, nucleotide insertions, and short inversions of nucleotide stretches. These modifications result in novel DNA sequences which encode CX3Ckine antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant CX3Ckine derivatives include predetermined or site-specific mutations of the respective protein or its fragments. "Mutant CX3Ckine" encompasses a polypeptide otherwise falling within the homology definition of the human CX3Ckine as set forth above, but having an amino acid sequence which differs from that of a CX3Ckine as found in nature, whether by way of deletion, substitution, or insertion. In particular, "site specific mutant CX3Ckine" generally includes proteins having significant similarity with a protein having a sequence of SEQ ID NO: 2, 4, 6, or 8, and as sharing various biological activities, e.g., antigenic or immunogenic, with those sequences, and in preferred embodiments contain most or all of the disclosed sequence. This applies also to polymorphic variants from different individuals. Similar concepts apply to different CX3Ckine proteins, particularly those found in various warm blooded animals, e.g., mammals and birds. As stated before, it is emphasized that descriptions are generally meant to encompass other CX3Ckine proteins, not limited to the human or mouse embodiments specifically discussed.

Although site specific mutation sites are predetermined, mutants need not be site specific. CX3Ckine mutagenesis can be conducted by making amino acid insertions or deletions. Substitutions, deletions, insertions, or any combinations may be generated to arrive at a final construct. These include amino acid residue substitution levels from none, one, two, three, five, seven, ten, twelve, fifteen, etc. Insertions include amino- or carboxyl-terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins, both the CX3Ckine, or antigen binding sites. A heterologous fusion protein is a fusion of proteins or segments which are naturally not normally fused in the same manner. Thus, the fusion product of an immunoglobulin with a CX3Ckine polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992. Thus, new chimeric polypeptides exhibiting new combinations of specificities will result from the functional linkage of protein-binding specificities and other functional domains.

VIII. Binding Agent:CX3Ckine Protein Complexes

A CX3Ckine protein that specifically binds to or that is specifically immunoreactive with an antibody generated against a defined immunogen, such as an immunogen consisting of the amino acid sequence of SEQ ID NO: 2, 4, 6, or 8, is typically determined in an immunoassay. The immunoassay uses a polyclonal antiserum which was raised to a protein of SEQ ID NO: 2, 4, 6, or 8. This antiserum is selected to have low crossreactivity against other chemokines and any such crossreactivity is removed by immunoabsorbtion prior to use in the immunoassay.

In order to produce antisera for use in an immunoassay, the protein of SEQ ID NO: 2, 4, 6, or 8, is isolated as described herein. For example, recombinant protein may be produced in a mammalian cell line. An inbred strain of mice such as balb/c is immunized with the protein of SEQ ID NO: 2, 4, 6, or 8, using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against C, C—C, and CXC chemokines, using a competitive binding immunoassay such as the one described in Harlow and Lane, supra, at pages 570-573. Preferably two chemokines are used in this determination in conjunction with either human CX3Ckine or mouse CX3Ckine.

In conjunction with a CX3Ckine, the monocyte chemotactic protein-1 (MCP-1) and macrophage inflammatory protein-1α (Mip-1α) are used to identify antibodies which are specifically bound by a CX3Ckine. In conjunction with human CX3Ckine, the monocyte chemotactic protein-2 (MCP-2) and Mip-1α are used to identify antibodies which are specifically bound by a CX3Ckine. These chemokines can be produced as recombinant proteins and isolated using standard molecular biology and protein chemistry techniques as described herein.

Immunoassays in the competitive binding format can be used for the crossreactivity determinations. For example, a protein of SEQ ID NO: 2. 4, 6, or 8 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2. 4, 6, or 8. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the CX3Ckine chemokine motif of SEQ ID NO: 2. 4, 6, or 8). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 that is required, then the second protein is said to specifically bind to an antibody generated to the immunogen.

It is understood that CX3Ckine proteins are a family of homologous proteins that comprise two or more genes. For a particular gene product, such as the human CX3Ckine protein, the term refers not only to the amino acid sequences disclosed herein, but also to other proteins that are polymorphic, allelic, non-allelic, or species variants. It is also understood that the term "human CX3Ckine" or "mouse CX3Ckine" includes normatural mutations introduced by deliberate mutation using conventional recombinant technology such as single site mutation, or by excising short sections of DNA encoding CX3Ckine proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring CX3Ckine protein, for example, the human CX3Ckine protein shown in SEQ ID NO: 2 or 4. The biological properties of the altered proteins can be determined by expressing the protein in an appropriate cell line and measuring, e.g., a chemotactic effect. Particular protein modifications considered minor would include conservative substitution of amino acids with similar chemical properties, as described above for the CX3Ckine family as a whole. By aligning a protein optimally with the protein of SEQ ID NO: 2. 4, 6, or 8, and by using the conventional immunoassays described herein to determine immunoidentity, or by using lymphocyte chemotaxis assays, one can determine the protein compositions of the invention.

IX. Functional Variants

The blocking of physiological response to CX3Ckines may result from the inhibition of binding of the protein to its receptor, e.g., through competitive inhibition. Thus, in vitro assays of the present invention will often use isolated protein, membranes from cells expressing a recombinant membrane associated CX3Ckine, soluble fragments comprising receptor binding segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or receptor fragments compete with a test compound for binding to the protein. In this manner, the antibodies can be used to detect the presence of a polypeptide which shares one or more antigenic binding sites of the protein and can also be used to occupy binding sites on the protein that might otherwise interact with a receptor.

"Derivatives" of CX3Ckine antigens include amino acid sequence mutants, glycosylation variants, and covalent or aggregate conjugates with other chemical moieties. Covalent derivatives can be prepared by linkage of functionalities to groups which are found in CX3Ckine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. See, e.g., Coligan, et al. (eds.) (1995 and periodic supplements) *Current Protocols in Protein Science*, John Wiley and Sons, New York, N.Y. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the CX3Ckine or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between CX3Ckines and other homologous or heterologous proteins are also provided. Many growth factors and cytokines are homodimeric entities, and a repeat construct may have various advantages, including lessened susceptibility to proteolytic degradation. Moreover, many receptors require dimerization to transduce a signal, and various dimeric proteins or domain repeats can be desirable. Heterologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., See, e.g., Dawson, et al. (1994) *Science* 266:776-779; and Godowski, et al. (1988) *Science* 241: 812-816. In particular, fusion proteins with portions from the related genes will be useful. Similar concepts of fusions with antigen binding sites are contemplated.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of CX3Ckines other than variations in amino acid sequence or glycosylation. Such derivatives may involve covalent or aggregative association with chemical moieties. These derivatives include: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a CX3Ckine antigen can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-CX3Ckine antibodies or its receptor. The CX3Ckines can also be labeled with a detectable group, e.g., radioiodinated by the chloramine T procedure, covalently bound to rare earth chelates, or conjugated to another fluorescent moiety for use in diagnostic assays. Purification of CX3Ckines may be effected by immobilized antibodies or receptor.

Isolated CX3Ckine genes will allow transformation of cells lacking expression of corresponding CX3Ckines, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of CX3Ckine receptor proteins. Subcellular fragments, e.g., cytoplasts or membrane fragments, can be isolated and used.

X. Uses

The present invention provides reagents which will find use in diagnostic applications as described elsewhere herein, e.g., in the general description for developmental abnormalities, or below in the description of kits for diagnosis.

CX3Ckine nucleotides, e.g., human or mouse CX3Ckine DNA or RNA, may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from CX3Ckine sequences may be used in in situ assays to detect chromosomal abnormalities. For instance, rearrangements in the mouse chromosome encoding a CX3Ckine gene may be detected via well-known in situ techniques, using CX3Ckine probes in conjunction with other known chromosome markers.

Antibodies and other binding agents directed towards CX3Ckine proteins or nucleic acids may be used to purify the corresponding CX3Ckine molecule. As described in the Examples below, antibody purification of CX3Ckine components is both possible and practicable. Antibodies and other binding agents may also be used in a diagnostic fashion to determine whether CX3Ckine components are present in a tissue sample or cell population using well-known techniques described herein. The ability to attach a binding agent to a CX3Ckine provides a means to diagnose disorders associated with CX3Ckine misregulation. Antibodies and other CX3Ckine binding agents may also be useful as histological markers. As described in the examples below, CX3Ckine expression is limited to specific tissue types. By directing a probe, such as an antibody or nucleic acid to a CX3Ckine it is possible to use the probe to distinguish tissue and cell types in situ or in vitro.

This invention also provides reagents with significant therapeutic value. The CX3Ckines (naturally occurring or recombinant), fragments thereof, and antibodies thereto, along with compounds identified as having binding affinity to a CX3Ckine, are useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a CX3Ckine is a target for an agonist or antagonist of the protein. The proteins likely play a role in regulation or development of neuronal or hematopoietic cells, e.g., lymphoid cells, which affect immunological responses.

Other abnormal developmental conditions are known in cell types shown to possess CX3Ckine mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the neuronal or immune system, cause significant medical abnormalities and conditions which may be susceptible to prevention or treatment using compositions provided herein.

Certain chemokines have also been implicated in viral replication mechanisms. See, e.g., Cohen (1996) *Science* 272:809-810; Feng, et al. (1996) *Science* 272:872-877; and Cocchi, et al. (1995) *Science* 270:1811-1816. The CX3C chemokine may be useful in a similar context. Alternatively, the stalk structure may be very important in presentation of the ligand domain, and other chemokines may be advantageously substituted for the chemokine domain in this molecule. Modification in the "stalk" structure may affect many of the pharmacological properties of the CX3Ckine, including half-life and biological activity.

Recombinant CX3Ckine or CX3Ckine antibodies can be purified and then administered to a patient, e.g., in sterile form. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to CX3Ckines, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity can activate the receptor and is thus an agonist in that it simulates the activity of a CX3Ckine. This invention further contemplates the therapeutic use of antibodies to CX3Ckines as antagonists. This approach should be particularly useful with other CX3Ckine species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 µM concentrations, usually less than about 100 nM, preferably less than about 10 µM (picomolar), and most preferably less than about 1 fM (femtomolar), with an appropriate carrier. Slow release formulations, or a slow release apparatus will often be utilized for continuous administration.

CX3Ckines, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, NY; Lieberman, et al. (eds.) (1990) *Pharmaceutical Dosage Forms: Tablets* Dekker, NY; and Lieberman, et al. (eds.) (1990) *Pharmaceutical Dosage Forms: Disperse Systems* Dekker, NY. The therapy of this invention may be combined with or used in association with other therapeutic agents.

Both the naturally occurring and the recombinant forms of the CX3Ckines of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, and other descriptions of chemical diversity libraries, which describe means for testing of binding affinity by a plurality of compounds. The development of suitable assays can be greatly facilitated by the availability of large amounts of purified, soluble CX3Ckine as provided by this invention.

For example, antagonists can normally be found once the protein has been structurally defined. Testing of potential protein analogs is now possible upon the development of highly automated assay methods using a purified receptor. In particular, new agonists and antagonists will be discovered by using screening techniques described herein. Of particular importance are compounds found to have a combined binding affinity for multiple CX3Ckine receptors, e.g., compounds which can serve as antagonists for species variants of a CX3Ckine.

This invention is particularly useful for screening compounds by using recombinant protein in a variety of drug screening techniques. The advantages of using a recombinant protein in screening for specific ligands include: (a) improved renewable source of the CX3Ckine from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a CX3Ckine receptor. Cells may be isolated which express a receptor in isolation from any others. Such cells, either in viable or fixed form, can be used for standard ligand/receptor binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses. Competitive assays are particularly useful, where the cells (source of CX3Ckine) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on CX3Ckine mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of a CX3Ckine. These cells are stably transformed with DNA vectors directing the expression of a CX3Ckine, e.g., an engineered membrane bound form. Essentially, the membranes would be prepared from the cells and used in a receptor/ligand binding assay such as the competitive assay set forth above.

Still another approach is to use solubilized, unpurified or solubilized, purified CX3Ckine from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a CX3Ckine antibody and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified CX3Ckine antibody, and washed. The next step involves detecting bound CX3Ckine antibody.

Rational drug design may also be based upon structural studies of the molecular shapes of the CX3Ckine and other effectors or analogs. See, e.g., *Methods in Enzymology* vols 202 and 203. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

A purified CX3Ckine can be coated directly onto plates for use in the aforementioned drug screening techniques. However, non-neutralizing antibodies to these ligands can be used as capture antibodies to immobilize the respective ligand on the solid phase.

XI. Kits

This invention also contemplates use of CX3Ckine proteins, fragments thereof, peptides, and their fusion products in a variety of diagnostic kits and methods for detecting the presence of CX3Ckine or a CX3Ckine receptor. Typically the kit will have a compartment containing either a defined CX3Ckine peptide or gene segment or a reagent which recognizes one or the other, e.g., receptor fragments or antibodies.

A kit for determining the binding affinity of a test compound to a CX3Ckine would typically comprise a test compound; a labeled compound, e.g., a receptor or antibody having known binding affinity for the CX3Ckine; a source of CX3Ckine (naturally occurring or recombinant); and a means for separating bound from free labeled compound, such as a solid phase for immobilizing the CX3Ckine. Once compounds are screened, those having suitable binding affinity to the CX3Ckine can be evaluated in suitable biological assays, as are well known in the art, to determine whether they act as agonists or antagonists to the receptor. The availability of recombinant CX3Ckine polypeptides also provide well defined standards for calibrating such assays.

A preferred kit for determining the concentration of, for example, a CX3Ckine in a sample would typically comprise a labeled compound, e.g., receptor or antibody, having known binding affinity for the CX3Ckine, a source of CX3Ckine (naturally occurring or recombinant), and a means for separating the bound from free labeled compound, for example, a solid phase for immobilizing the CX3Ckine. Compartments containing reagents, and instructions, will normally be provided.

Antibodies, including antigen binding fragments, specific for the CX3Ckine or ligand fragments are useful in diagnostic applications to detect the presence of elevated levels of CX3Ckine and/or its fragments. Such may allow diagnosis of the amounts of differently processed forms of the CX3Ckine, e.g., successively degraded stalk structure. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-CX3Ckine complex) or heterogeneous (with a separation step). Various commercial assays exist, such as radioimmunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a CX3Ckine or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY.

Anti-idiotypic antibodies may have similar use to diagnose presence of antibodies against a CX3Ckine, as such may be diagnostic of various abnormal states. For example, overproduction of CX3Ckine may result in production of various immunological or other medical reactions which may be diagnostic of abnormal physiological states, e.g., in cell growth, activation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled CX3Ckine is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or noncovalently joining a moiety which directly or indirectly provides a detectable signal. In any of these assays, the protein, test compound, CX3Ckine, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The CX3Ckine can be immobilized on various matrices followed by washing. Suitable matrices include plastic such as an ELISA plate, filters, and beads. Methods of immobilizing the CX3Ckine to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a CX3Ckine. These sequences can be used as probes for detecting levels of the CX3Ckine message in samples from natural sources, or patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

XII. Receptor Isolation

Having isolated a binding partner of a specific interaction, methods exist for isolating the counter-partner. See, Gearing, et al. (1989) *EMBO J.* 8:3667-3676. For example, means to label a CX3Ckine without interfering with the binding to its receptor can be determined. For example, an affinity label or epitope tag can be fused to either the amino- or carboxyl-terminus of the ligand. An expression library can be screened for specific binding of the CX3Ckine, e.g., by cell sorting, or other screening to detect subpopulations which express such a binding component. See, e.g., Ho, et al. (1993) *Proc. Nat'l Acad. Sci. USA* 90:11267-11271. Alternatively, a panning method may be used. See, e.g., Seed and Aruffo (1987) *Proc. Nat'l Acad. Sci. USA* 84:3365-3369. A two-hybrid selection system may also be applied making appropriate constructs with the available BAS-1 sequences. See, e.g., Fields and Song (1989) *Nature* 340:245-246.

Protein cross-linking techniques with label can be applied to isolate binding partners of a CX3Ckine. This would allow identification of proteins which specifically interact with a CX3Ckine, e.g., in a ligand-receptor like manner. Typically, the chemokine family binds to receptors of the seven transmembrane receptor family, and the receptor for the CX3Ckine is likely to exhibit a similar structure. Thus, it is likely that the receptor will be found by expression in a system which is capable of expressing such a membrane protein in a form capable of exhibiting ligand binding capability.

The broad scope of this invention is best understood with reference to the following examples, which are not intended to limit the invention to specific embodiments.

Examples

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1-3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; Crowe, et al. (1992) *QIAexpress: The High Level Expression & Protein Purification System* QIAGEN, Inc., Chatsworth, Calif.; and Coligan, et al. (eds.) (1995 and periodic supplements) *Current Protocols in Protein Science*, John Wiley and Sons, New York, N.Y.

Standard immunological techniques are described, e.g., in Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of Human CX3Ckine Clone

A clone encoding the human CX3Ckine is isolated from a natural source by many different possible methods. Given the sequences provided herein, PCR primers or hybridization probes are selected and/or constructed to isolate either genomic DNA segments or cDNA reverse transcripts. Appropriate cell sources include human tissues, e.g., brain libraries. Tissue distribution below also suggests source tissues. Genetic and polymorphic or allelic variants are isolated by screening a population of individuals.

PCR based detection is performed by standard methods, preferably using primers from opposite ends of the coding sequence, but flanking segments might be selected for specific purposes.

Alternatively, hybridization probes are selected. Particular AT or GC contents of probes are selected depending upon the expected homology and mismatching expected. Appropriate stringency conditions are selected to balance an appropriate positive signal to background ratio. Successive washing steps are used to collect clones of greater homology.

Further clones are isolated using an antibody based selection procedure. Standard expression cloning methods are applied including, e.g., FACS staining of membrane associated expression product. The antibodies are used to identify clones producing a recognized protein. Alternatively, antibodies are used to purify a CX3C chemokine, with protein sequencing and standard means to isolate a gene encoding that protein.

Genomic sequence based methods will also allow for identification of sequences naturally available, or otherwise, which exhibit homology to the provided sequences. Similar procedures will allow isolation of other primate genes.

III. Isolation of Rodent CX3Ckine Clone

Similar methods are used as above to isolate an appropriate mouse CX3C chemokine gene. Similar source materials as indicated above are used to isolate natural genes, including genetic, polymorphic, allelic, or strain variants. Species variants are also isolated using similar methods, e.g., from rats, moles, muskrats, copybaras, etc.

IV. Isolation of an avian CX3Ckine clone

An appropriate avian source is selected as above. Similar methods are utilized to isolate a species variant, though the level of similarity will typically be lower for avian CX3C chemokine as compared to a human to mouse sequence.

V. Expression; Purification; Characterization

With an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purification.

With a clone encoding a vertebrate CX3C chemokine, recombinant production means are used, although natural forms may be purified from appropriate sources. The protein product is purified by standard methods of protein purification, in certain cases, e.g., coupled with immunoaffinity methods. Immunoaffinity methods are used either as a purification step, as described above, or as a detection assay to determine the separation properties of the protein.

Preferably, the protein is secreted into the medium, and the soluble product is purified from the medium in a soluble form. Alternatively, as described above, inclusion bodies from prokaryotic expression systems are a useful source of material. Typically, the insoluble protein is solubilized from the inclusion bodies and refolded using standard methods. Purification methods are developed as described above.

In certain embodiments, the protein is made in a eukaryotic cell which glycosylates the protein normally. The purification methods may be affected thereby, as may biological activities. The intact protein can be processed to release the chemokine domain, probably due to a protease cleavage event somewhere in the glycosylated stalk region close to the chemokine/stalk boundary. While recombinant protein appears to be processed, the physiological processes which normally do such in native cells remain to be determined.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods.

CX3C chemokine protein biochemistry was assessed in mammalian expression systems. Human embryonic kidney 293 cells (HEK 293) transfected with a mammalian expression construct encoding full-length CX3C chemokine were metabolically labeled with $^{35}$S cysteine and methionine. CX3C chemokine was produced as a protein of Mr ~95 kDa; control transfected supernatants contained no such species. Neuraminidase and gycosidases reduced the Mr of CX3C chemokine from ~95 kDa to ~45 kDa, suggesting that the recombinant form is glycosylated substantially. Thus CX3C chemokine cDNA, encoding a predicted membrane-bound protein, encodes a glycoprotein which is released from cells by an undefined mechanism.

Prediction of glycosylation sites may be made, e.g., as reported in Hansen, et al. (1995) *Biochem. J.* 308:801-813.

VI. Preparation of Antibodies Against Vertebrate CX3Ckine

With protein produce, as above, animals are immunized to produce antibodies. Polyclonal antiserum is raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments. Preferred fragments include the chemokine domain.

Polyclonal serum is raised against a purified antigen, purified as indicated above, or using synthetic peptides. A series of overlapping synthetic peptides which encompass all of the full length sequence, if presented to an animal, will produce serum recognizing most linear epitopes on the protein. Such an antiserum is used to affinity purify protein, which is, in turn, used to introduce intact full length protein into another animal to produce another antiserum preparation.

Similar techniques are used to generate induce monoclonal antibodies to either unpurified antigen, or, preferably, purified antigen.

VII. Cellular and Tissue Distribution

Distribution of the protein or gene products are determined, e.g., using immunohistochemistry with an antibody reagent, as produced above, or by screening for nucleic acids encoding the chemokine. Either hybridization or PCR methods are used to detect DNA, cDNA, or message content. Histochemistry allows determination of the specific cell types within a tissue which express higher or lower levels of message or DNA. Antibody techniques are useful to quantitate protein in a biological sample, including a liquid or tissue sample. Immunoassays are developed to quantitate protein.

Hybridization techniques were applied to the tissue types in Table 3 with positive or negative results, as indicated. The commercial tissue blots may have cellular contamination from resident cells, e.g., from blood or other cells which populate the tissue. The large and small transcripts correspond to sizes about 4 kb and less than about 2 kb, respectively.

TABLE 3

Tissue and cell distribution of human CX3Ckine gene.
Commercial tissue library:

| cell type | large | small |
|---|---|---|
| spleen | − | − |
| thymus | + | − |
| prostate | + | + |
| testis | + | − |
| ovary | + | − |
| small intestine | + | + |
| colon | + | + |
| peripheral blood | − | − |

Further analysis of tissue distribution indicates abundance of human message: heart +++; brain +++; placenta −; lung ++; liver −; muscle +; kidney −; pancreas +; spleen −; thymus +; prostate ++; testis +; ovary +; small intestine ++; colon ++; peripheral blood −; HL60 promyelocytic leukemia line −; HeLa cell S3−; K562 chronic myelogenous leukemia line −; Molt4 lymphoblastic leukemia line −; Burkitts lymphoma RAJI line −; SW480 colorectal adenocarcinoma line +; A549 lung carcinoma line −; and G361 melanoma line −.

"Reverse northerns" are blots from cDNA libraries with the inserts removed, and the size determinations are based upon the size of inserts in the cDNA library, and reflect the lengths found in the cDNA library inserts, which may be less than full length where the reverse transcription was not full length. As such, size determinations there are not reflective of the natural sizes. The results of these are: PBMC (peripheral blood mononuclear cells) +; PBMC (activated using T cell stimulation conditions, with anti-CD3 and PMA) −; Mot72 (resting Th0 clone) +; Mot 72 (activated with anti-CD28 and anti-CD3) −; Mot72 α (activated with anti-peptide, anergic clone) −; Mot81 (resting Th0 clone) −; Mot81 (activated with anti-CD28 and anti-CD3) −; HY06 (resting Th1 clone) −; HY06 (activated with anti-CD28 and anti-CD3) −; HY06α (activated with anti-peptide, anergic clone) −; HY935 (resting Th2 clone) −; HY935 (activated with anti-CD28 and anti-CD3) +; BC pool of EBV transformed lines +; resting splenocytes +; splenocytes +(activated using B cell stimulating conditions, with anti-CD40 and IL-4) −; NK cell pool −; NK pool (activated 6 h with PMA and ionomycin) +; NKA6 NK cell clone −; NKB1 NK cell clone −; NK non-cytotoxic cell clone +; and NK clone stimulated to be cytotoxic Other cells and tissues: CHO cells +; Jurkat cells (DNAX) +; Jurkat cells (another source) +; normal T cell pool +; TCT pool (transformed T cells) −; fetal kidney −; fetal lung −; fetal liver −; fetal heart −; fetal brain +; fetal gall bladder +; fetal small intestine +; fetal adipose +; fetal ovary −; fetal uterus +; adult placenta −; fetal testis +; fetal spleen +; and fetal brain +. Additional cells provided: U937 (resting monocyte cell line) +; C— (elutriated monocyte activated with LPS, IFN-γ, and anti-IL-10) +; C+(elutriated monocytes activated with LPS, IFN-γ, and IL-10) +; M1 (elutriated monocytes activated with LPS1 h)+; M6 (elutriated monocytes activated with LPS 6 h) +; 30% DC (resting 30% CD1a+ dendritic cells, proliferated in TNF-α and GM-CSF)+; 70% DC (resting 70% CD1a+ dendritic cells, proliferated in TNF-α and GM-CSF) +; D1 (dendritic cells stimulated 1 h in PMA and ionomycin)−; D6 (dendritic cells stimulated 6 h in PMA and ionomycin) −; D5 DC (resting dendritic cells cultured 5 d in GM-CSF and IL-4) +; DC (dendritic cells cultured in GM-CSF and IL-4, LPS activated) +; DC (GM-CSF activated, like D5 cells) +; DC mix (dendritic cells stimulated with a mixture of cytokines) +; CD1a+(99% pure CD1a+ dendritic cells, enriched from 70% DC) +; CD14+ (CD14+ fraction sorted from 70% DC, monocyte-like morphology) −; CD1Aa+ (95% CD1a+ and CD86+ sorted from 70% DC) −; TF1 (hematopoietic precursor line) +; Jurkat (T cell line)+; MRC5 (lung fibroblast sarcoma cell line) +; JY (B cell line) +; U937 (pre-monocytic cell line) +.

Since the endothelium is a major site of chemokine action, a northern blot was performed to ascertain if CX3Ckine was expressed in this tissue. Human CX3Ckine was also shown to be expressed on human activated primary endothelial cells by both mRNA and protein expression. This suggests that CX3Ckine may be involved in leukocyte trafficking in various organs.

In summary, human CX3Ckine mRNA is found in monocytes, dendritic cells, T cells and B cells, e.g., found in certain immune cells.

VIII. Microchemotaxis Assays

The pro-migratory activities of CX3C chemokine have been assessed in microchemotaxis assays. See, e.g., Bacon, et al. (1988) *Br. J. Pharmacol.* 95:966-974. CX3C chemokine appears to be a potent attractant of peripheral blood monocytes and T cells. Pro-migratory activity for blood neutrophils has been difficult to demonstrate.

IX. Chromosomal Mapping

The CX3C chemokine gene has been mapped to human chromosome 16. A BIOS Laboratories (New Haven, Conn.) mouse somatic cell hybrid panel was combined with PCR. These mapping studies also indicate the possibility of a pseudogene or related gene on human chromosome 14. Sequencing of genomic DNA fragments suggests CX3C chemokine gene has an intron which begins near or in the codon encoding Ile 64. Other intron/exon boundaries have yet to be mapped. This location is distinct from the chromosomal mapping locations of the other C, CC, or CXC chemokine families, consistent with the CX3Ckine being a separate gene family within the chemokines.

X. Biological Activities, Direct and Indirect

The 293 human embryonic kidney cell line (HEK 293) was transfected with either the membrane bound form of human CX3Ckine (293-CX3Ckine), the chemokine domain plus the "stalk" region, or a control vector without an insert. The transfected cells were subsequently cultured with either monocytes, T cells, or peripheral mononuclear (PMN) cells to assay relative adherence of these cells to CX3Ckine. Specifically, $5 \times 10^4$ cells per well of HEK 293 transfected cells were seeded in a 96 well plate. $2 \times 10^5$ monocytes, T cells, or PMNs, metabolically labeled with $^{35}$S-methionine and cysteine (Amersham, Arlington Heights, Ill.), were added to each well. The plate was then incubated at 37° C. for varius time points. The wells were washed 2 times RPMI supplemented with 1% FCS. Plates were then read in a Millipore Cytofluor at 485/530 nm.

In all cases, adherence to HEK 293 cells transfected with the membrane bound form of CX3Ckine was significantly enhanced when compared to the truncated CX3Ckine or mock transfected cells. Interestingly, only the membrane bound form possessed this proadhesive activity, leading to the conclusion that CX3Ckine, in its membrane bound form, may serve as a regulator of circulating leukocytes.

In another experiment, the recombinant soluble form of the chemokine domain of CX3Ckine (rCx3C) was added to HEK 293-CX3C cells and monocytes at a concentration of 1 μM per well, and assayed as described above. rCX3C was able to antagonize adhesion of monocytes to HEK 293-CX3C cells. A similar experiment was performed to investigate the effect on T cell adherence. Comparable results were obtained. Thus rCX3C may function as a negative regulator of circulating leukocytes.

A comparison of three different forms of human CX3Ckine was performed to analyze variations in chemoattractant activity that may be due to the structure of CX3Ckine. CX3C 1.7 (chemokine domain plus the entire stalk region), CX3C 0.7 (chemokine domain plus one-half stalk region), and CX3C CK (chemokine domain only) were subjected to the chemotaxicity assay described above, their ability to attract T cells was analyzed. CX3C 1.7 displayed a slightly better dose dependent ability to attract T cells relative to the other forms of CX3Ckine.

A robust and sensitive assay is selected as described above, e.g., on immune cells, neuronal cells, or stem cells. Chemokine is added to the assay in increasing doses to see if a dose response is detected. For example, in a proliferation assay, cells are plated out in plates. Appropriate culture medium is provided, and chemokine is added to the cells in varying amounts. Growth is monitored over a period of time which will detect either a direct effect on the cells, or an indirect effect of the chemokine.

Alternatively, an activation assay or attraction assay is used. An appropriate cell type is selected, e.g, hematopoietic cells, myeloid (macrophages, neutrophils, polymorphonuclear cells, etc.) or lymphoid (T cell, B cell, or NK cells), neural cells (neurons, neuroglia, oligodendrocytes, astrocytes, etc.), or stem cells, e.g., progenitor cells which differentiate to other cell types, e.g., gut crypt cells and undifferentiated cell types.

Other assays will be those which have been demonstrated with other chemokines. See, e.g., Schall and Bacon (1994) *Current Opinion in Immunology* 6:865-873; and Bacon and Schall (1996) *Int. Arch. Allergy & Immunol.* 109:97-109. Effects of truncated stalk structures will be similarly evaluated.

XI. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analysed, e.g., by PCR analysis and sequencing. This allows evaluation of population polymorphisms. Particularly, as described above, many of the biological activities of the chemokine domain attached to different portions or extents of the stalk structure may result.

XII. Screening for Agonists/Antagonists

Agonists or antagonists are screened for ability to induce or block biological activity. The candidate compounds, e.g, sequence variants of natural CX3Ckines, are assayed for their biological activities. Alternatively, compounds are screened, alone or in combinations, to determine effects on biological activity.

XIII. Isolation of a Receptor for CX3C Chemokine

Based on the proadherent properties of CX3Ckine, 7 transmembrane G-protein receptor was found to be expressed by monocytes and T cells. It was also discovered that the chemokine domain is the only region of CX3Ckine that can engage the receptor. Binding assays with known chemokine receptor revealed that CX3Ckine does not engage chemokine receptors CCR 1 through 5, CXCR 1 and 2, or the Duffy antigen receptor. CX3Ckine can, however, bind to a virally encoded chemokine receptor, CMV-US28.

Alternatively, CX3C chemokine can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods. The typical chemokine receptor is a seven transmembrane receptor.

The purified protein is also be used to identify other binding partners of CX3Ckine as described, e.g., in Fields and Song (1989) *Nature* 340:245-246.

The binding composition, e.g., chemokine, is used to screen an expression library made from a cell line which expresses a binding partner, i.e. receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J.* 10:2821-2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3 \times 10^5$ cells per chamber in 1.5 ml of growth media. Incubate overnight at 37 C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of human CX3C chemokine cDNA at 1 and 1/200 dilution, and a negative mock. Rinse cells with serum free DME. Add the DNA solution and incubate 5 hr at 37 C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80 C after all liquid is removed. For each chamber, 0.5 ml incubations are performed as follows. Add HBSS/saponin (0.1%) with 32 µl/ml of 1 M $NaN_3$ for 20 min. Cells are then washed with HBSS/saponin 1×. Add chemokine or chemokine/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85-90 C.

Evaluate positive staining of pools and pregressively subclone to isolation of single genes responsible for the binding.

Alternatively, chemokine reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a chemokine fusion construct, or by use of antibodies raised against the first antibodies. Recursive cycles of selection and amplification lead to enrichment of appropriate clones and eventual isolation of receptor expressing clones. Phage expression libraries can be screened by chemokine. Appropriate label techniques, e.g., anti-FLAG antibodies, will allow specific labeling of appropriate clones.

SEQUENCES

SEQ ID NO: 1 is human CX3Ckine nucleotide sequence.
SEQ ID NO: 2 is human CX3Ckine amino acid sequence.
SEQ ID NO: 3 is more complete human CX3Ckine nucleotide sequence.
SEQ ID NO: 4 is more complete human CX3Ckine amino acid sequence.
SEQ ID NO: 5 is partial mouse CX3Ckine nucleotide sequence.
SEQ ID NO: 6 is partial mouse CX3Ckine amino acid sequence.
SEQ ID NO: 7 is complete mouse CX3Ckine nucleotide sequence.
SEQ ID NO: 8 is complete mouse CX3C amino acid sequence.
SEQ ID NO: 9 is Gro amino acid sequence.
SEQ ID NO: 10 is Ltn amino acid sequence.
SEQ ID NO: 11 is MIP-10 amino acid sequence.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A method for blocking binding of a CX3C chemokine polypeptide to a cell that expresses a receptor for the chemokine; wherein said chemokine polypeptide
   a) chemoattracts peripheral blood monocytes or T-cells,
   b) consists of an amino acid sequence comprising at least 95% amino acid sequence identity to the amino acid sequence set forth in SEQ ID NO: 8, and
   c) comprises a chemokine domain identical to residues 25 to 100 of the amino acid sequence set forth in SEQ ID NO: 8; comprising contacting said chemokine polypeptide with an antibody or antigen-binding fragment thereof that specifically binds to said chemokine polypeptide.

2. The method of claim 1 wherein said antibody or antigen-binding fragment thereof is detectably labeled.

3. The method of claim 1 wherein said antibody or antigen-binding fragment thereof is a polyclonal antibody.

4. The method of claim 1 wherein said antibody or antigen-binding fragment thereof is a monoclonal antibody.

5. The method of claim 1 wherein said antibody or antigen-binding fragment thereof is a Fab.

6. The method of claim 1 wherein said antibody or antigen-binding fragment thereof is a F(ab)$_2$.

* * * * *

SEQUENCE LISTING

```
<160> NUMBER OF SEQ ID NOS: 11

<210> SEQ ID NO 1
<211> LENGTH: 534
<212> TYPE: DNA
<213> ORGANISM: Homo sapiens
<220> FEATURE:
<221> NAME/KEY: CDS
<222> LOCATION: (89)..(424)
<220> FEATURE:
<221> NAME/KEY: misc_feature
<222> LOCATION: (462)..(462)
<223> OTHER INFORMATION: n is a, c, g, or t
<220> FEATURE:
```

<221> NAME/KEY: misc_feature
<222> LOCATION: (520)..(520)
<223> OTHER INFORMATION: n is a, c, g, or t

<400> SEQUENCE: 1

```
cccaagcttg gcacgagggc actgagctct gccgcctggc tctagccgcc tgcctggccc        60
ccgccgggac tcttgcccac cctcagcc atg gct ccg ata tct ctg tcg tgg         112
                                Met Ala Pro Ile Ser Leu Ser Trp
                                  1               5 ctg ctc cgc ttg gcc acc ttc tgc cat ctg act gtc ctg ctg gct gga        160
Leu Leu Arg Leu Ala Thr Phe Cys His Leu Thr Val Leu Leu Ala Gly
 10                  15                  20 cag cac cac ggt gtg acg aaa tgc aac atc acg tgc agc aag atg aca        208
Gln His His Gly Val Thr Lys Cys Asn Ile Thr Cys Ser Lys Met Thr
 25                  30                  35                  40 tca aag ata cct gta gct ttg ctc atc cac tat caa cag aac cag gca        256
Ser Lys Ile Pro Val Ala Leu Leu Ile His Tyr Gln Gln Asn Gln Ala
                 45                  50                  55 tca tgc ggc aaa cgc gca atc atc ttg gag acg aga cag cac agg ctg        304
Ser Cys Gly Lys Arg Ala Ile Ile Leu Glu Thr Arg Gln His Arg Leu
             60                  65                  70 ttc tgt gcc gac ccg aag gag caa tgg gtc aag gac gcg atg cag cat        352
Phe Cys Ala Asp Pro Lys Glu Gln Trp Val Lys Asp Ala Met Gln His
 75                  80                  85 ctg gac cgc cag gct gct gcc cta act ccg aaa tgg cgg cac ctt ccg        400
Leu Asp Arg Gln Ala Ala Ala Leu Thr Pro Lys Trp Arg His Leu Pro
         90                  95                 100 aag aag cca gat cgg cga ggt tga agcccaggac caccccctgc cgccggggga       454
Lys Lys Pro Asp Arg Arg Gly
105                 110 aatgacnag tctgttggtc cctggaaccc cgaaagccca caggcgaaaa gccagttacc       514
ctgganccga atccttcttc                                                   534
```

<210> SEQ ID NO 2
<211> LENGTH: 111
<212> TYPE: PRT
<213> ORGANISM: Homo sapiens

<400> SEQUENCE: 2

```
Met Ala Pro Ile Ser Leu Ser Trp Leu Leu Arg Leu Ala Thr Phe Cys
  1               5                  10                  15

His Leu Thr Val Leu Leu Ala Gly Gln His His Gly Val Thr Lys Cys
                 20                  25                  30

Asn Ile Thr Cys Ser Lys Met Thr Ser Lys Ile Pro Val Ala Leu Leu
             35                  40                  45

Ile His Tyr Gln Gln Asn Gln Ala Ser Cys Gly Lys Arg Ala Ile Ile
         50                  55                  60

Leu Glu Thr Arg Gln His Arg Leu Phe Cys Ala Asp Pro Lys Glu Gln
 65                  70                  75                  80

Trp Val Lys Asp Ala Met Gln His Leu Asp Arg Gln Ala Ala Ala Leu
                 85                  90                  95

Thr Pro Lys Trp Arg His Leu Pro Lys Pro Asp Arg Arg Gly
                100                 105                 110
```

<210> SEQ ID NO 3
<211> LENGTH: 1654
<212> TYPE: DNA
<213> ORGANISM: Homo sapiens
<220> FEATURE:
<221> NAME/KEY: CDS

<222> LOCATION: (86)..(1279)

<400> SEQUENCE: 3

```
aagcttggca cgagggcact gagctctgcc gcctggctct agccgcctgc ctggcccccg      60
ccgggactct tgcccaccct cagcc atg gct ccg ata tct ctg tcg tgg ctg      112
                            Met Ala Pro Ile Ser Leu Ser Trp Leu
                              1               5 ctc cgc ttg gcc acc ttc tgc cat ctg act gtc ctg ctg gct gga cag      160
Leu Arg Leu Ala Thr Phe Cys His Leu Thr Val Leu Leu Ala Gly Gln
 10              15                  20                  25 cac cac ggt gtg acg aaa tgc aac atc acg tgc agc aag atg aca tca      208
His His Gly Val Thr Lys Cys Asn Ile Thr Cys Ser Lys Met Thr Ser
             30                  35                  40 aag ata cct gta gct ttg ctc atc cac tat caa cag aac cag gca tca      256
Lys Ile Pro Val Ala Leu Leu Ile His Tyr Gln Gln Asn Gln Ala Ser
         45                  50                  55 tgc ggc aaa cgc gca atc atc ttg gag acg aga cag cac agg ctg ttc      304
Cys Gly Lys Arg Ala Ile Ile Leu Glu Thr Arg Gln His Arg Leu Phe
     60                  65                  70 tgt gcc gac ccg aag gag caa tgg gtc aag gac gcg atg cag cat ctg      352
Cys Ala Asp Pro Lys Glu Gln Trp Val Lys Asp Ala Met Gln His Leu
 75                  80                  85 gac cgc cag gct gct gcc cta act cga aat ggc ggc acc ttc gag aag      400
Asp Arg Gln Ala Ala Ala Leu Thr Arg Asn Gly Gly Thr Phe Glu Lys
 90                  95                 100                 105 cag atc ggc gag gtg aag ccc agg acc acc cct gcc gcc ggg gga atg      448
Gln Ile Gly Glu Val Lys Pro Arg Thr Thr Pro Ala Ala Gly Gly Met
             110                 115                 120 gac gag tct gtg gtc ctg gag ccc gaa gcc aca ggc gaa agc agt agc      496
Asp Glu Ser Val Val Leu Glu Pro Glu Ala Thr Gly Glu Ser Ser Ser
         125                 130                 135 ctg gag ccg act cct tct tcc cag gaa gca cag agg gcc ctg ggg acc      544
Leu Glu Pro Thr Pro Ser Ser Gln Glu Ala Gln Arg Ala Leu Gly Thr
     140                 145                 150 tcc cca gag ctg ccg acg ggc gtg act ggt tcc tca ggg acc agg ctc      592
Ser Pro Glu Leu Pro Thr Gly Val Thr Gly Ser Ser Gly Thr Arg Leu
 155                 160                 165 ccc ccg acg cca aag gct cag gat gga ggg cct gtg ggc acg gag ctt      640
Pro Pro Thr Pro Lys Ala Gln Asp Gly Gly Pro Val Gly Thr Glu Leu
170                 175                 180                 185 ttc cga gtg cct ccc gtc tcc act gcc gcc acg tgg cag agt tct gct      688
Phe Arg Val Pro Pro Val Ser Thr Ala Ala Thr Trp Gln Ser Ser Ala
             190                 195                 200 ccc cac caa cct ggg ccc agc ctc tgg gct gag gca aag acc tct gag      736
Pro His Gln Pro Gly Pro Ser Leu Trp Ala Glu Ala Lys Thr Ser Glu
         205                 210                 215 gcc ccg tcc acc cag gac ccc tcc acc cag gcc tcc act gcg tcc tcc      784
Ala Pro Ser Thr Gln Asp Pro Ser Thr Gln Ala Ser Thr Ala Ser Ser
     220                 225                 230 cca gcc cca gag gag aat gct ccg tct gaa ggc cag cgt gtg tgg ggt      832
Pro Ala Pro Glu Glu Asn Ala Pro Ser Glu Gly Gln Arg Val Trp Gly
 235                 240                 245 cag gga cag agc ccc agg cca gag aac tct ctg gag cgg gag gag atg      880
Gln Gly Gln Ser Pro Arg Pro Glu Asn Ser Leu Glu Arg Glu Glu Met
250                 255                 260                 265 ggt ccc gtg cca gcg cac acg gat gcc ttc cag gac tgg ggg cct ggc      928
Gly Pro Val Pro Ala His Thr Asp Ala Phe Gln Asp Trp Gly Pro Gly
             270                 275                 280 agc atg gcc cac gtc tct gtg gtc cct gtc tcc tca gaa ggg acc ccc      976
Ser Met Ala His Val Ser Val Val Pro Val Ser Ser Glu Gly Thr Pro
```

```
                     285                 290                 295
agc agg gag cca gtg gct tca ggc agc tgg acc cct aag gct gag gaa    1024
Ser Arg Glu Pro Val Ala Ser Gly Ser Trp Thr Pro Lys Ala Glu Glu
        300                 305                 310 ccc atc cat gcc acc atg gac ccc cag agg ctg ggc gtc ctt atc act    1072
Pro Ile His Ala Thr Met Asp Pro Gln Arg Leu Gly Val Leu Ile Thr
    315                 320                 325 cct gtc cct gac gcc cag gct gcc acc cgg agg cag gcg gtg ggg ctg    1120
Pro Val Pro Asp Ala Gln Ala Ala Thr Arg Arg Gln Ala Val Gly Leu
330                 335                 340                 345 ctg gcc ttc ctt ggc ctc ctc ttc tgc ctg ggg gtg gcc atg ttc acc    1168
Leu Ala Phe Leu Gly Leu Leu Phe Cys Leu Gly Val Ala Met Phe Thr
                350                 355                 360 tac cag agc ctc cag ggc tgc cct cga aag atg gca gga gag atg gcg    1216
Tyr Gln Ser Leu Gln Gly Cys Pro Arg Lys Met Ala Gly Glu Met Ala
            365                 370                 375 gag ggc ctt cgc tac atc ccc cgg agc tgt ggt agt aat tca tat gtc    1264
Glu Gly Leu Arg Tyr Ile Pro Arg Ser Cys Gly Ser Asn Ser Tyr Val
        380                 385                 390 ctg gtg ccc gtg tga actcctctgg cctgtgtcta gttgtttgat tcagacagct    1319
Leu Val Pro Val
    395 gcctgggatc cctcatcctc atacccaccc ccacccaagg gcctggcctg agctgggatg    1379 attggagggg ggaggtggga tcctccaggt gcacaagctc caagctccca ggcattcccc    1439 aggaggccag ccttgaccat tctccacctt ccagggacag aggggtggc ctcccaactc    1499 accccagccc caaaactctc ctctgctgct ggctggttag aggttccctt tgacgccatc    1559 ccagccccaa tgaacaatta tttattaaat gcccagcccc ttctgaaaaa aaaaaaaaa    1619 aaaaaaaaaa aaaaaaaaaa aattcctgcg gccgc                                1654

<210> SEQ ID NO 4
<211> LENGTH: 397
<212> TYPE: PRT
<213> ORGANISM: Homo sapiens

<400> SEQUENCE: 4

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
                20                  25                  30

Asn Ile Thr Cys Ser Lys Met Thr Ser Lys Ile Pro Val Ala Leu Leu
            35                  40                  45

Ile His Tyr Gln Gln Asn Gln Ala Ser Cys Gly Lys Arg Ala Ile Ile
        50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160
```

```
Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395

<210> SEQ ID NO 5
<211> LENGTH: 209
<212> TYPE: DNA
<213> ORGANISM: Mus sp.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: CDS
<222> LOCATION: (63)..(209)
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t

<400> SEQUENCE: 5
```

-continued

```
tnactactag gagctgcgac acggcccagc ctcctggccc gncgaattcc tgcactccag    60
```

| cc atg gct ccc tcg ccg ctc gcg tgg ctg ctg cgc ctg gcc gcg ttc | 107 |
|---|---|
| Met Ala Pro Ser Pro Leu Ala Trp Leu Leu Arg Leu Ala Ala Phe | |
| 1               5                  10                 15 | |

| ttc cat ttg tgt act ctg ctg ccg ggt nag cac ctc ggc atg acg aaa | 155 |
|---|---|
| Phe His Leu Cys Thr Leu Leu Pro Gly Xaa His Leu Gly Met Thr Lys | |
|             20                 25                 30 | |

| tgc gaa atc atg tgc gac aag atg acc tna cga atn cca gtg gct tta | 203 |
|---|---|
| Cys Glu Ile Met Cys Asp Lys Met Thr Xaa Arg Xaa Pro Val Ala Leu | |
|     35                 40                 45 | |

| ntc atc | 209 |
|---|---|
| Xaa Ile | |

<210> SEQ ID NO 6
<211> LENGTH: 49
<212> TYPE: PRT
<213> ORGANISM: Mus sp.
<220> FEATURE:
<221> NAME/KEY: misc_feature
<222> LOCATION: (25)..(25)
<223> OTHER INFORMATION: The 'Xaa' at location 25 stands for Lys, Glu,
      or Gln.
<220> FEATURE:
<221> NAME/KEY: misc_feature
<222> LOCATION: (41)..(41)
<223> OTHER INFORMATION: The 'Xaa' at location 41 stands for Ser, or
      Leu.
<220> FEATURE:
<221> NAME/KEY: misc_feature
<222> LOCATION: (43)..(43)
<223> OTHER INFORMATION: The 'Xaa' at location 43 stands for Ile, or
      Met.
<220> FEATURE:
<221> NAME/KEY: misc_feature
<222> LOCATION: (48)..(48)
<223> OTHER INFORMATION: The 'Xaa' at location 48 stands for Ile, Val,
      Leu, or Phe.

<400> SEQUENCE: 6

Met Ala Pro Ser Pro Leu Ala Trp Leu Leu Arg Leu Ala Ala Phe Phe
1               5                   10                  15

His Leu Cys Thr Leu Leu Pro Gly Xaa His Leu Gly Met Thr Lys Cys
            20                  25                  30

Glu Ile Met Cys Asp Lys Met Thr Xaa Arg Xaa Pro Val Ala Leu Xaa
        35                  40                  45

Ile

<210> SEQ ID NO 7
<211> LENGTH: 3065
<212> TYPE: DNA
<213> ORGANISM: Mus sp.
<220> FEATURE:
<221> NAME/KEY: CDS
<222> LOCATION: (62)..(1249)

<400> SEQUENCE: 7

```
tgactactag gagctgcgac acggcccagc ctcctggccg ccgaattcct gcactccagc    60
```

| c atg gct ccc tcg ccg ctc gcg tgg ctg ctg cgc ctg gcc gcg ttc ttc | 109 |
|---|---|
| Met Ala Pro Ser Pro Leu Ala Trp Leu Leu Arg Leu Ala Ala Phe Phe | |
| 1               5                   10                  15 | |

| cat ttg tgt act ctg ctg ccg ggt cag cac ctc ggc atg acg aaa tgc | 157 |
|---|---|
| His Leu Cys Thr Leu Leu Pro Gly Gln His Leu Gly Met Thr Lys Cys | |
|             20                  25                  30 | |

| gaa atc atg tgc ggc aag atg acc tca cga atc cca gtg gct ttg ctc | 205 |
|---|---|
| Glu Ile Met Cys Gly Lys Met Thr Ser Arg Ile Pro Val Ala Leu Leu | |
|         35                  40                  45 | |

| | |
|---|---|
| atc cgc tat cag cta aat cag gag tcc tgc ggc aag cgt gcc att gtc<br>Ile Arg Tyr Gln Leu Asn Gln Glu Ser Cys Gly Lys Arg Ala Ile Val<br>50                        55                      60 | 253 |
| ctg gag acg aca cag cac aga cgc ttc tgt gct gac ccg aag gag aaa<br>Leu Glu Thr Thr Gln His Arg Arg Phe Cys Ala Asp Pro Lys Glu Lys<br>65                        70                      75                      80 | 301 |
| tgg gtc caa gac gcc atg aag cat ctg gat cac cag gct gct gcc ctc<br>Trp Val Gln Asp Ala Met Lys His Leu Asp His Gln Ala Ala Ala Leu<br>                      85                      90                      95 | 349 |
| act aaa aat ggt ggc aag ttt gag aag cgg gtg gac aat gtg aca cct<br>Thr Lys Asn Gly Gly Lys Phe Glu Lys Arg Val Asp Asn Val Thr Pro<br>                100                      105                      110 | 397 |
| ggg atc acc ttg gcc act agg gga ctg tcc cca tct gcc ctg aca aag<br>Gly Ile Thr Leu Ala Thr Arg Gly Leu Ser Pro Ser Ala Leu Thr Lys<br>                115                      120                      125 | 445 |
| cct gaa tcc gcc aca ttg gaa gac ctt gct ttg gaa ctg act act att<br>Pro Glu Ser Ala Thr Leu Glu Asp Leu Ala Leu Glu Leu Thr Thr Ile<br>130                        135                      140 | 493 |
| tcc cag gag gcc agg ggg acc atg ggg act tcc caa gag cca ccg gca<br>Ser Gln Glu Ala Arg Gly Thr Met Gly Thr Ser Gln Glu Pro Pro Ala<br>145                        150                      155                      160 | 541 |
| gca gtg acc gga tca tct ctc tca act tcc gag gca cag gat gca ggg<br>Ala Val Thr Gly Ser Ser Leu Ser Thr Ser Glu Ala Gln Asp Ala Gly<br>                165                      170                      175 | 589 |
| ctt acg gct aag cct cag agc att gga agt ttt gag gcg gct gac atc<br>Leu Thr Ala Lys Pro Gln Ser Ile Gly Ser Phe Glu Ala Ala Asp Ile<br>                180                      185                      190 | 637 |
| tcc acc acc gtt tgg ccg agt cct gct gtc tac caa tct gga tct agc<br>Ser Thr Thr Val Trp Pro Ser Pro Ala Val Tyr Gln Ser Gly Ser Ser<br>                195                      200                      205 | 685 |
| tcc tgg gct gag gaa aaa gct act gag tcc ccc tcc act aca gcc cca<br>Ser Trp Ala Glu Glu Lys Ala Thr Glu Ser Pro Ser Thr Thr Ala Pro<br>210                        215                      220 | 733 |
| tct cct cag gtg tcc act act tca cct tca acc cca gag gaa aat gtt<br>Ser Pro Gln Val Ser Thr Thr Ser Pro Ser Thr Pro Glu Glu Asn Val<br>225                        230                      235                      240 | 781 |
| ggg tcc gaa ggc caa ccc cca tgg gtc cag gga cag gac ctc agt cca<br>Gly Ser Glu Gly Gln Pro Pro Trp Val Gln Gly Gln Asp Leu Ser Pro<br>                      245                      250                      255 | 829 |
| gag aag tct cta ggg tct gag gag ata aac cca gtt cat act gat aat<br>Glu Lys Ser Leu Gly Ser Glu Glu Ile Asn Pro Val His Thr Asp Asn<br>                      260                      265                      270 | 877 |
| ttc cag gag agg ggg cct ggc aac aca gtc cac ccc tca gtg gct ccc<br>Phe Gln Glu Arg Gly Pro Gly Asn Thr Val His Pro Ser Val Ala Pro<br>                      275                      280                      285 | 925 |
| atc tcc tct gaa gag acc ccc agc cca gag ctg gtg gcc tcg ggc agc<br>Ile Ser Ser Glu Glu Thr Pro Ser Pro Glu Leu Val Ala Ser Gly Ser<br>290                        295                      300 | 973 |
| cag gct cct aag ata gag gaa ccc atc cat gcc act gca gat ccc cag<br>Gln Ala Pro Lys Ile Glu Glu Pro Ile His Ala Thr Ala Asp Pro Gln<br>305                        310                      315                      320 | 1021 |
| aaa ctg agt gtg ctt atc act cct gtc ccc gac acc cag gca gcc aca<br>Lys Leu Ser Val Leu Ile Thr Pro Val Pro Asp Thr Gln Ala Ala Thr<br>                      325                      330                      335 | 1069 |
| agg agg cag gca gtg ggg cta ctg gct ttc ctt ggt ctt ctt ttc tgc<br>Arg Arg Gln Ala Val Gly Leu Leu Ala Phe Leu Gly Leu Leu Phe Cys<br>                      340                      345                      350 | 1117 |
| cta ggg gtg gcc atg ttt gct tac cag agc ctt cag ggc tgt ccc cgc<br>Leu Gly Val Ala Met Phe Ala Tyr Gln Ser Leu Gln Gly Cys Pro Arg<br>                      355                      360                      365 | 1165 |

```
aaa atg gcg ggg gaa atg gta gaa ggc ctc cgc tac gtc ccc cgt agc    1213
Lys Met Ala Gly Glu Met Val Glu Gly Leu Arg Tyr Val Pro Arg Ser
    370                 375                 380 tgt ggc agt aac tca tac gtc ctg gtg cca gtg tga gctgcttgcc         1259
Cys Gly Ser Asn Ser Tyr Val Leu Val Pro Val
385                 390                 395 tgcctgcctg tgtccagagt gtgattcgga cagctgtctg ggaccccccc cccatcctca  1319
tacccacctt catccacgct ggggaaatgg gaatggagaa gctggacctc caggggctgt  1379
gggctccatc caatcccct tcccccgagg ggtggcccg gaggccaccc tagaccacta    1439
ttcacttatc agagacagag caggtgacct tccagctcct ctatatttga aagaatcctc  1499
tgctgctggc tggttagagg ggcccttgac accccaactc cagtgaacaa ttatttattg  1559
gattcccagc ccctgcgacg acacctgttt cccgcgcgca ccgtggtccg cccatatcac  1619
aagcagcagg ccaggcctat ctgcctgtcc ccctgacctc cttgtgtctc ctggctttgc  1679
tgcagtcgcc agcccttctc ctcccgcc agccgcggtg ctatctgccc tatgtctccc    1739
tctatcccct gtacagagcg caccaccatc accatcaaca ccgctgttgt gtcttttctt  1799
gcatgaggtt aaagctgtgt tttctggagc tctccgggaa gggagacaag cttgcgagag  1859
ggtttaaagt gttcctcccc agacttggat gtgctgtgag gcatgctgc gtctgaagga   1919
agggtccagt ccccactcgg ctaccagcac cacaaagtgc cccacctgta aaggaaaga   1979
aacgtggtcc agagctggca ataacctatg gccctgacat catcactttc tctgagatcc  2039
ttgtctccac ccctgggtgc aaccccaccc cttatcaaca ttaatagtca ctgccattcc  2099
actggactga catttttgta ccctgtgatt ctgagggctg gcaaggagtg gcttgagagt  2159
gcagatcgta ccctgtatgc cccccccaaa tggaggctga gttggggact tgcaggaaca  2219
gaggccaact cagatggctt cccctgtgtt ctcactagaa accctcccc catgcaccaa   2279
ggtgacagtc acaggtctgc cctggctaaa ggacaagcca cataggaaag attaggacaa  2339
gcccctcgga ggcagaggat ccagggtaaa ccctggagt ggccacaaac ccaatttcag   2399
tgtagggact tgtgcatgtg tgtacttgca tagtcagaca gaggctgcca gggtcctttc  2459
ctgtctctga gagcagtgtt cacgccaagg actcaccttt gccccattg caggcagggc   2519
cagaactccc atagcattct ccaagagccc tgtgacattt tctggaagga actctgccct  2579
gggcgcaaag tgactgctga agcaaggagc agctgagcag caccccagcg gagctgagcc  2639
ggcaggccac gcccctcggg gggggcatt tctacccgcc ctgctctgaa tagctccaac   2699
ttcaccttag gagcctccca ggggcgagct tcacccagaa gccagtgact cactccttga  2759
ttggtggaag ctcagttggc tcctgagagt gaggaagcca acctttgtc gaccctcctc   2819
ctgggaagcc tgtgggcggc tctgatcatg ctccacagaa ccagttgtag gcctgagccg  2879
cagcagcccg agtgcactat atcctggctc cttcggtggg gaaccttaa gggttgggac   2939
acccgtcatc ggactttgtt ggttcctccc tcccagcaga gaatgtgggc cgtaacaatc  2999
tgaggaggac tttaaaagtt gttgatcctt tagggtttt tttcaagcat cattaccaat   3059
gtctgt                                                             3065
```

<210> SEQ ID NO 8
<211> LENGTH: 395
<212> TYPE: PRT
<213> ORGANISM: Mus sp.

<400> SEQUENCE: 8

Met Ala Pro Ser Pro Leu Ala Trp Leu Leu Arg Leu Ala Ala Phe Phe

```
              1               5                  10                 15
His Leu Cys Thr Leu Leu Pro Gly Gln His Leu Gly Met Thr Lys Cys
                      20                  25                  30

Glu Ile Met Cys Gly Lys Met Thr Ser Arg Ile Pro Val Ala Leu Leu
                      35                  40                  45

Ile Arg Tyr Gln Leu Asn Gln Glu Ser Cys Gly Lys Arg Ala Ile Val
 50                      55                  60

Leu Glu Thr Thr Gln His Arg Arg Phe Cys Ala Asp Pro Lys Glu Lys
 65                      70                  75                  80

Trp Val Gln Asp Ala Met Lys His Leu Asp His Gln Ala Ala Ala Leu
                      85                  90                  95

Thr Lys Asn Gly Gly Lys Phe Glu Lys Arg Val Asp Asn Val Thr Pro
                     100                 105                 110

Gly Ile Thr Leu Ala Thr Arg Gly Leu Ser Pro Ser Ala Leu Thr Lys
                     115                 120                 125

Pro Glu Ser Ala Thr Leu Glu Asp Leu Ala Leu Glu Leu Thr Thr Ile
                     130                 135                 140

Ser Gln Glu Ala Arg Gly Thr Met Gly Thr Ser Gln Glu Pro Pro Ala
145                      150                 155                 160

Ala Val Thr Gly Ser Ser Leu Ser Thr Ser Glu Ala Gln Asp Ala Gly
                     165                 170                 175

Leu Thr Ala Lys Pro Gln Ser Ile Gly Ser Phe Glu Ala Ala Asp Ile
                     180                 185                 190

Ser Thr Thr Val Trp Pro Ser Pro Ala Val Tyr Gln Ser Gly Ser Ser
                     195                 200                 205

Ser Trp Ala Glu Glu Lys Ala Thr Glu Ser Pro Ser Thr Thr Ala Pro
                     210                 215                 220

Ser Pro Gln Val Ser Thr Thr Ser Pro Ser Thr Pro Glu Glu Asn Val
225                      230                 235                 240

Gly Ser Glu Gly Gln Pro Pro Trp Val Gln Gly Gln Asp Leu Ser Pro
                     245                 250                 255

Glu Lys Ser Leu Gly Ser Glu Glu Ile Asn Pro Val His Thr Asp Asn
                     260                 265                 270

Phe Gln Glu Arg Gly Pro Gly Asn Thr Val His Pro Ser Val Ala Pro
                     275                 280                 285

Ile Ser Ser Glu Glu Thr Pro Ser Pro Glu Leu Val Ala Ser Gly Ser
                     290                 295                 300

Gln Ala Pro Lys Ile Glu Glu Pro Ile His Ala Thr Ala Asp Pro Gln
305                      310                 315                 320

Lys Leu Ser Val Leu Ile Thr Pro Val Pro Asp Thr Gln Ala Ala Thr
                     325                 330                 335

Arg Arg Gln Ala Val Gly Leu Leu Ala Phe Leu Gly Leu Leu Phe Cys
                     340                 345                 350

Leu Gly Val Ala Met Phe Ala Tyr Gln Ser Leu Gln Gly Cys Pro Arg
                     355                 360                 365

Lys Met Ala Gly Glu Met Val Glu Gly Leu Arg Tyr Val Pro Arg Ser
                     370                 375                 380

Cys Gly Ser Asn Ser Tyr Val Leu Val Pro Val
385                      390                 395

<210> SEQ ID NO 9
<211> LENGTH: 96
<212> TYPE: PRT
<213> ORGANISM: Artificial Sequence
<220> FEATURE:
```

<223> OTHER INFORMATION: Gro amino acid sequence

<400> SEQUENCE: 9

```
Met Ile Pro Ala Thr Arg Ser Leu Leu Cys Ala Ala Leu Leu Leu
1               5                   10                  15

Ala Thr Ser Arg Leu Ala Thr Gly Ala Pro Ile Ala Asn Glu Leu Arg
            20                  25                  30

Cys Gln Cys Leu Gln Thr Met Ala Gly Ile His Leu Lys Asn Ile Gln
            35                  40                  45

Ser Leu Lys Val Leu Pro Ser Gly Pro His Cys Thr Gln Thr Glu Val
        50                  55                  60

Ile Ala Thr Leu Lys Asn Gly Arg Glu Ala Cys Leu Asp Pro Glu Ala
65                  70                  75                  80

Pro Leu Val Gln Lys Ile Val Gln Lys Met Leu Lys Gly Val Pro Lys
                85                  90                  95
```

<210> SEQ ID NO 10
<211> LENGTH: 115
<212> TYPE: PRT
<213> ORGANISM: Artificial Sequence
<220> FEATURE:
<223> OTHER INFORMATION: Ltn amino acid sequence

<400> SEQUENCE: 10

```
Met Arg Leu Leu Leu Thr Phe Leu Gly Val Cys Cys Leu Thr Pro
1               5                   10                  15

Trp Val Glu Gly Val Gly Thr Glu Val Leu Glu Glu Ser Ser Cys
            20                  25                  30

Val Asn Leu Gln Thr Gln Arg Leu Pro Val Gln Lys Ile Lys Thr Tyr
            35                  40                  45

Ile Ile Trp Glu Gly Ala Met Arg Ala Val Ile Phe Val Thr Lys Arg
        50                  55                  60

Gly Leu Lys Ile Cys Ala Asp Pro Glu Ala Lys Trp Val Leu Ala Ala
65                  70                  75                  80

Ile Lys Thr Val Asp Gly Arg Ala Ser Thr Arg Lys Asn Met Ala Glu
                85                  90                  95

Thr Val Pro Gly Thr Gly Ala Gln Arg Ser Thr Ser Thr Ala Ile Thr
            100                 105                 110

Leu Thr Gly
        115
```

<210> SEQ ID NO 11
<211> LENGTH: 92
<212> TYPE: PRT
<213> ORGANISM: Artificial Sequence
<220> FEATURE:
<223> OTHER INFORMATION: Mip-1 beta amino acid sequence

<400> SEQUENCE: 11

```
Met Lys Leu Cys Val Ser Ala Leu Ser Leu Leu Leu Val Ala Ala
1               5                   10                  15

Phe Cys Ala Pro Gly Phe Ser Ala Pro Met Gly Ser Asp Pro Thr
            20                  25                  30

Ser Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
        50                  55                  60

Phe Gln Thr Lys Arg Ser Lys Gln Val Cys Ala Asp Pro Ser Glu Ser
65                  70                  75                  80
```

```
Trp Val Gln Glu Tyr Val Tyr Asp Leu Glu Leu Asn
                85                  90
```